US011229397B2

(12) United States Patent
Garcia Molina et al.

(10) Patent No.: US 11,229,397 B2
(45) Date of Patent: Jan. 25, 2022

(54) SYSTEM AND METHOD FOR OUTPUTTING AN INDICATOR REPRESENTATIVE OF THE EFFECTS OF STIMULATION PROVIDED TO A SUBJECT DURING SLEEP

(71) Applicant: KONINKLIJKE PHILIPS N.V., Eindhoven (NL)

(72) Inventors: Gary Nelson Garcia Molina, Madison, WI (US); Tsvetomira Kirova Tsoneva, Eindhoven (NL); Stefan Pfundtner, Eindhoven (NL); Surya Subrahmanya Sreeram Vissapragada Venkata Satya, Monroeville, PA (US); Anandi Mahadevan, Murrysville, PA (US); Diane Kosobud, Montgomery, OH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 226 days.

(21) Appl. No.: 16/470,791

(22) PCT Filed: Dec. 21, 2017

(86) PCT No.: PCT/EP2017/084078
§ 371 (c)(1),
(2) Date: Jun. 18, 2019

(87) PCT Pub. No.: WO2018/115277
PCT Pub. Date: Jun. 28, 2018

(65) Prior Publication Data
US 2019/0343455 A1 Nov. 14, 2019

Related U.S. Application Data

(60) Provisional application No. 62/437,973, filed on Dec. 22, 2016.

(51) Int. Cl.
*A61B 5/00* (2006.01)
*A61B 5/048* (2006.01)
(Continued)

(52) U.S. Cl.
CPC ............ *A61B 5/4815* (2013.01); *A61B 5/374* (2021.01); *A61B 5/4812* (2013.01);
(Continued)

(58) Field of Classification Search
CPC ..... A61B 5/4812; A61B 5/4815; A61B 5/374; A61B 5/4848; A61B 5/4836;
(Continued)

(56) References Cited

U.S. PATENT DOCUMENTS 10,137,276 B2 11/2018 Garcia Molina et al.
10,183,142 B2 1/2019 Garcia Molina et al.
(Continued)

FOREIGN PATENT DOCUMENTS

WO 2015118415 A1 8/2015

OTHER PUBLICATIONS

International Search Report and Written Opinion, International Application No. PCT/EP2017/084078, dated Apr. 17, 2018.
(Continued)

*Primary Examiner* — Christine H Matthews
*Assistant Examiner* — Joshua Daryl D Lannu

(57) ABSTRACT

The present disclosure pertains to a system configured to output an indicator representative of effects of stimulation provided to a subject during a sleep session. The indicator is determined based on a combination of the effect of stimulation on sleep restoration, stimulation quality, sleep architecture factors, and/or other information. The indicator is determined using age matched reference information on deep sleep duration and EEG slow wave activity. The contribution to the indicator associated with sleep architec-
(Continued)

ture factors is determined based on age matched reference information including sleep onset latency, wake after sleep onset, total sleep time, micro-arousal count, sleep stage(s) prior to awakening, and/or other information.

14 Claims, 18 Drawing Sheets

(51) Int. Cl.
    *A61M 21/02*     (2006.01)
    *A61B 5/374*     (2021.01)
    *A61M 21/00*     (2006.01)

(52) U.S. Cl.
    CPC ........... *A61B 5/4848* (2013.01); *A61M 21/02* (2013.01); *A61B 5/4836* (2013.01); *A61M 2021/0027* (2013.01); *A61M 2230/10* (2013.01)

(58) Field of Classification Search
    CPC .............. A61M 2230/10; A61M 21/02; A61M 2021/0027; A61M 2230/005
    See application file for complete search history.

(56) References Cited

U.S. PATENT DOCUMENTS

| | | |
|---|---|---|
| 10,220,183 B2 | 3/2019 | Garcia Molina et al. |
| 2007/0213786 A1* | 9/2007 | Sackellares ........ A61N 1/36025 607/45 |
| 2007/0276439 A1* | 11/2007 | Miesel ................. A61B 5/4818 607/2 |
| 2016/0151603 A1 | 6/2016 | Shouldice et al. |
| 2016/0296164 A1 | 10/2016 | Garcia Molina |
| 2016/0302718 A1 | 10/2016 | Lapoint et al. |

OTHER PUBLICATIONS

Ngo, H et al., "Induction of slow oscillations by rhythmic acoustic stimulation.," J. Sleep Res., p. 10 pp, Aug. 2012.
H.-V. V Ngo, T. Martinetz, J. Born, and M. Molle, "Auditory Closed-Loop Stimulation of the Sleep Slow Oscillation Enhances Memory," Neuron, vol. 78, No. May, pp. 1-9, 2013.
M. Bellesi, B. A. Riedner, G. Garcia-Molina, C. Cirelli, and G. Tononi, "Enhancement of sleep slow waves: underlying mechanisms and practical consequences," Front. Syst. Neurosci., vol. 8, No. October, pp. 1-17, Oct. 2014.
G. Santostasi, R. Malkani, B. A. Riedner, M. Bellesi, G. Tononi, K. A. Paller, and P. C. Zee, "Phase-locked loop for precisely timed acoustic stimulation during sleep," J. Neurosci. Methods, pp. 1-14, 2015.
B. A. Riedner, B. K. Hulse, F. Ferrarelli, S. Sarasso, and G. Tononi, "Enhancing sleep slow waves with natural stimuli," Medicamundi, vol. 45, No. 2, pp. 82-88, 2010.
G. Tononi and C. Cirelli, "Sleep and the price of plasticity: from synaptic and cellular homeostasis to memory consolidation and integration.," Neuron, vol. 81, No. 1, pp. 12-34, Jan. 2014.
M. M. Ohayon, M. a Carskadon, C. Guilleminault, and M. V Vitiello, "Meta-analysis of quantitative sleep parameters from childhood to old age in healthy individuals: developing normative sleep values across the human lifespan," Sleep, vol. 27, No. 7, pp. 1255-1273, 2004.

* cited by examiner (A)

(B)

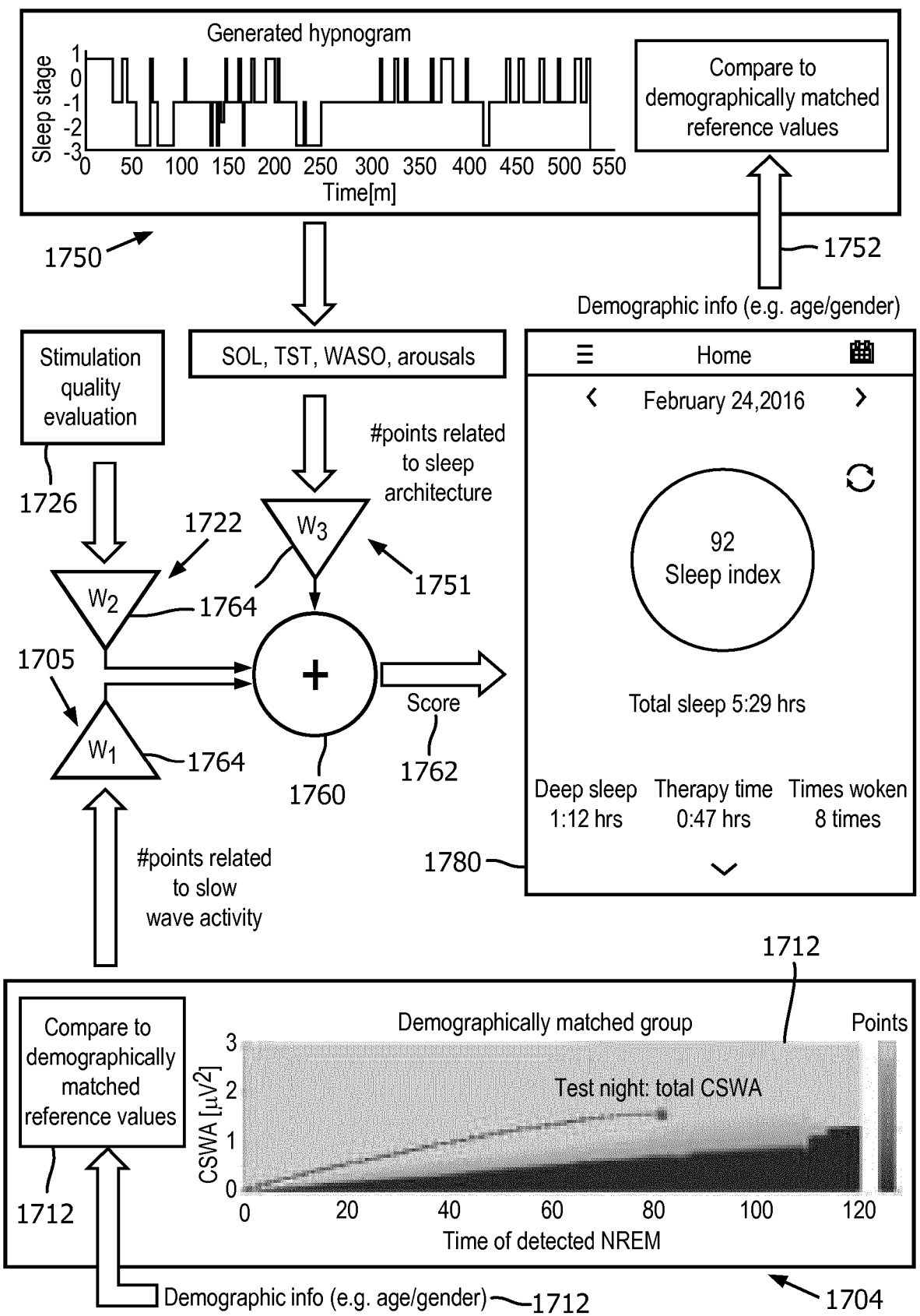
FIG. 17 continue

SYSTEM AND METHOD FOR OUTPUTTING AN INDICATOR REPRESENTATIVE OF THE EFFECTS OF STIMULATION PROVIDED TO A SUBJECT DURING SLEEP

CROSS-REFERENCE TO PRIOR APPLICATIONS

This application is the U.S. National Phase application under 35 U.S.C. § 371 of International Application Serial No. PCT/EP2017/084078, filed on 21 Dec. 2017, which claims the benefit of U.S. application Ser. No. 62/437,973, filed on 22 Dec. 2016. These applications are hereby incorporated by reference herein.

BACKGROUND

1. Field

The present disclosure pertains to a system and method for outputting an indicator representative of effects of stimulation provided to a subject during a sleep session.

2. Description of the Related Art

Systems for monitoring sleep are known. The restorative value of sleep can be increased by delivering appropriately timed auditory stimulation during deep sleep to enhance sleep slow waves. Typically, systems for monitoring sleep do not automatically generate an output that informs a user of the benefits of stimulation provided during a sleep session. The present disclosure overcomes deficiencies in prior art systems.

SUMMARY

Accordingly, one or more aspects of the present disclosure relate to a system configured to output an indicator representative of effects of stimulation provided to a subject during a sleep session. The system comprises one or more stimulators, one or more sensors, one or more hardware processors, and/or other components. The one or more stimulators are configured to provide the stimulation to the subject during the sleep session. The one or more sensors are configured to generate output signals conveying information related to brain activity in the subject during the sleep session. The one or more hardware processors operatively communicate with the one or more stimulators and the one or more sensors. The one or more hardware processors are configured by machine-readable instructions to determine, based on the output signals and the stimulation provided to the subject: a slow wave activity metric indicative of a cumulative amount of slow wave activity in the subject during the sleep session; a stimulation quality metric indicative how well the stimulation enhances slow wave activity in the subject during the sleep session; and a sleep architecture metric indicative of a sleep quality for the subject during the sleep session. The one or more hardware processors are configured to combine the slow wave activity metric, the stimulation quality metric, and the sleep architecture metric to determine the indicator; and output the indicator for display to the subject.

Yet another aspect of the present disclosure relates to a method for outputting an indicator representative of effects of stimulation provided to a subject during a sleep session with an indicator system. The system comprises one or more stimulators, one or more sensors, one or more hardware processors, and/or other components. The method comprises: providing, with the one or more stimulators, the stimulation to the subject during the sleep session; generating, with the one or more sensors, output signals conveying information related to brain activity in the subject during the sleep session; and determining, with the one or more processors, based on the output signals and the stimulation provided to the subject: a slow wave activity metric indicative of a cumulative amount of slow wave activity in the subject during the sleep session; a stimulation quality metric indicative how well the stimulation enhances slow wave activity in the subject during the sleep session; and a sleep architecture metric indicative of a sleep quality for the subject during the sleep session. The method comprises combining, with the one or more processors, the slow wave activity metric, the stimulation quality metric, and the sleep architecture metric to determine the indicator; and outputting, with the one or more hardware processors, the indicator for display to the subject.

Still another aspect of present disclosure relates to a system for a system for outputting an indicator representative of effects of stimulation provided to a subject during a sleep session. The system comprises: means for providing the stimulation to the subject during the sleep session; means for generating output signals conveying information related to brain activity in the subject during the sleep session; and means for determining, based on the output signals and the stimulation provided to the subject: a slow wave activity metric indicative of a cumulative amount of slow wave activity in the subject during the sleep session; a stimulation quality metric indicative how well the stimulation enhances slow wave activity in the subject during the sleep session; and a sleep architecture metric indicative of a sleep quality for the subject during the sleep session. The system comprises means for combining the slow wave activity metric, the stimulation quality metric, and the sleep architecture metric to determine the indicator; and means for outputting the indicator for display to the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
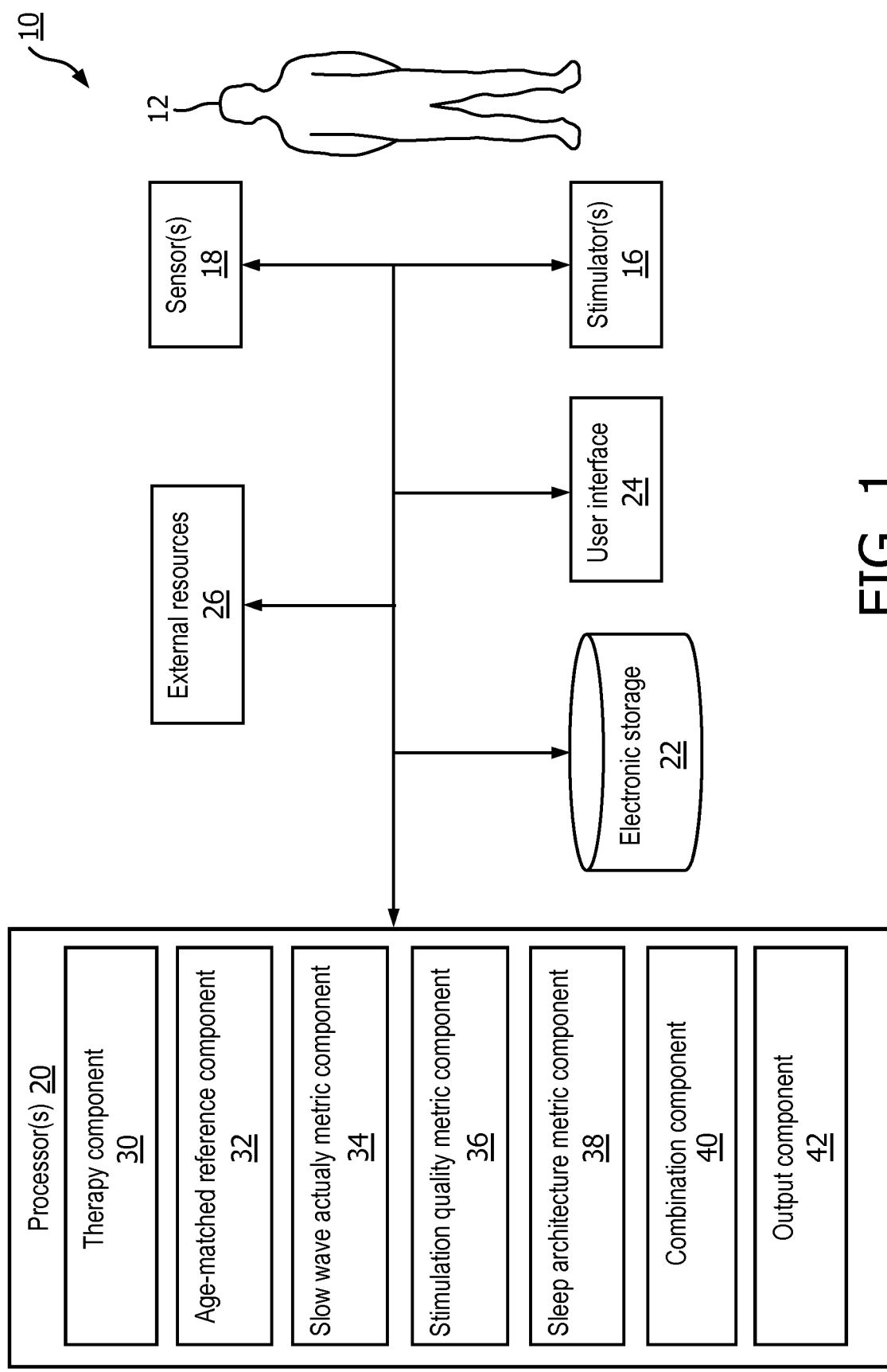
FIG. 1 illustrates a system configured to output an indicator representative of effects of stimulation provided to a subject during a sleep session.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to automatically output an indicator representative of effects of stimulation provided to a subject 12 during a sleep session. Typical systems that monitor sleep provide scores to users that describe sleep during a particular sleep session. However, the types of scores that are used in typical systems do not capture the benefits of sleep enhancement though stimulation because, regardless of whether they use actigraphy (e.g., Microsoft Band, Fitbit) or electroencephalography (e.g., Zeo) for example, these system focus on sleep architecture (or macro-sleep) parameters such as sleep stage percentages, micro-arousal counts, total sleep time, etc. System 10 is configured such that the indicator is determined based on, in addition to sleep architecture information, information related to slow wave activity (electroencephalogram (EEG) power in the 0.5 to 4 Hz band), information related to the quality of stimulation provided to subject 12, age matched reference information, and/or other information.

System 10 is configured to determine and combine individually weighted metrics related to slow wave activity, stimulation quality, sleep architecture, and/or other information to determine the indicator. For example, in some embodiments, system 10 is configured such that the metrics are individually weighted and the indicator comprises a score, a color coded display, and/or other indicators determined based on a combination of the individually weighted metrics. System 10 is configured such that the indicator (e.g., the score, the color coded display, etc.) is output for display to subject 12 and/or other users on a mobile computing device and/or other computing devices associated with subject 12, via system 10 (e.g., a display that is part of a user interface included in system 10), and/or on other devices.

In some embodiments, system 10 is configured such that the slow wave activity related metric quantifies a total amount of EEG power in one or more specific EEG power bands (e.g., as described below) throughout non-rapid eye movement (NREM) sleep. This is related to the restorative value of sleep and is influenced by the stimulation provided to subject 12 during a sleep session. In some embodiments, the stimulation quality related metric quantifies how well stimulation enhances slow wave activity in subject 12 during a sleep session. The stimulation quality related metric may also be indicative of an amount of stimulation subject 12 receives during a sleep session. The stimulation quality metric may be determined based on various properties of the stimulation (e.g., number of tones, maximum volume reached, average volume, etc.). In some embodiments, the sleep architecture related metric quantifies sleep quality based on parameters such as total sleep duration (TST), duration of wake after sleep onset (WASO), number of detected sleep micro-arousals, sleep onset latency (SOL), parameters related to the duration of sleep stages, and/or other parameters for subject 12.

System 10 is configured such that the individual metrics are determined based on age matched reference information related to slow wave activity, stimulation quality, sleep architecture, and/or other information for a population of subjects similar in age and/or other demographic characteristics to subject 12. The age matched reference information comprises statistical distributions of various parameters (e.g., as described herein) related to slow wave activity, stimulation quality, sleep architecture, and/or other information across the age matched population.

In some embodiments, system 10 includes one or more of a stimulator 16, a sensor 18, a processor 20, electronic storage 22, a user interface 24, external resources 26, and/or other components.

Stimulator 16 is configured to provide electric, magnetic, and/or sensory stimulation to subject 12. Stimulator 16 is configured to provide electric, magnetic, and/or sensory stimulation to subject 12 prior to a sleep session, during a sleep session, and/or at other times. For example, stimulator 16 may be configured to provide stimuli to subject 12 during a sleep session to facilitate a transition to a deeper stage of sleep, a lighter stage of sleep, maintain sleep in a specific stage, and/or for other purposes. In some embodiments, stimulator 16 may be configured such that facilitating a transition between deeper sleep stages and lighter sleep stages includes decreasing sleep slow waves in subject 12, and facilitating a transition between lighter sleep stages and deeper sleep stages includes increasing sleep slow waves.

Stimulator 16 is configured to facilitate transitions between sleep stages and/or maintain sleep in a specific stage through non-invasive brain stimulation and/or other methods. Stimulator 16 may be configured to facilitate transitions between sleep stages and/or maintain sleep in a specific stage through non-invasive brain stimulation using electric, magnetic, and/or sensory stimuli. The electric, magnetic, and/or sensory stimulation may include auditory stimulation, visual stimulation, somatosensory stimulation, electrical stimulation, magnetic stimulation, a combination of different types of stimulation, and/or other stimulation. The electric, magnetic, and/or sensory stimuli include odors, sounds, visual stimulation, touches, tastes, somato-sensory stimulation, haptic, electrical, magnetic, and/or other stimuli. For example, acoustic tones may be provided to subject 12 to facilitate transitions between sleep stages and/or maintain sleep in a specific stage. Examples of stimulator 16 may include one or more of a sound generator, a speaker, a music player, a tone generator, one or more electrodes on the scalp of subject 12, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, stimulator 16 is configured to adjust the intensity, timing, and/or other parameters of the stimulation provided to subject 12.

Sensor 18 is configured to generate output signals conveying information related to brain activity, activity of the central nervous system, activity of the peripheral nervous system, and/or other activity in subject 12. In some embodiments, the information related to brain activity includes the information related to the central nervous system, the information related to the activity of the peripheral nervous system, and/or other information. In some embodiments, sensor 18 is configured to generate output signals conveying information related to slow wave activity in subject 12. In some embodiments, the information related to brain activity, activity of the central nervous system, activity of the peripheral nervous system, and/or other activity in subject 12 is the information related to slow wave activity. In some embodiments, sensor 18 is configured to generate output signals conveying information related to stimulation provided to subject 12 during sleep sessions.

In some embodiments, the slow wave activity of subject 12 may correspond to a sleep stage of subject 12. The sleep stage of subject 12 may be associated with rapid eye movement (REM) sleep, NREM sleep, and/or other sleep. The sleep stage of subject 12 may be one or more of NREM stage N1, stage N2, or stage N3, sleep, REM sleep, and/or other sleep stages. In some embodiments, NREM stage 3 and/or 4 may be slow wave (e.g., deep) sleep. Sensor 18 may comprise one or more sensors that measure such parameters directly. For example, sensor 18 may include EEG electrodes configured to detect electrical activity along the scalp of subject 12 resulting from current flows within the brain of subject 12. Sensor 18 may comprise one or more sensors that generate output signals conveying information related to slow wave activity of subject 12 indirectly. For example, one or more sensors 18 may comprise a heart rate sensor that generates an output based on a heart rate of subject 12 (e.g., sensor 18 may be a heart rate sensor than can be located on the chest of subject 12, and/or be configured as a bracelet on a wrist of subject 12, and/or be located on another limb of subject 12), movement of subject 12 (e.g., sensor 18 may comprise an accelerometer that can be carried on a wearable, such as a bracelet around the wrist and/or ankle of subject 12 such that sleep may be analyzed using actigraphy signals), respiration of subject 12, and/or other characteristics of subject 12.

In some embodiments, the one or more sensors comprise one or more of the EEG electrodes, an electrooculogram (EOG) electrode, an actigraphy sensor, an electrocardiogram (EKG) electrode, a respiration sensor, a pressure sensor, a vital signs camera, a photoplethysmogram (PPG) sensor, a functional near infra-red sensor (fNIR), a temperature sensor, a microphone and/or other sensors configured to generate output signals related to (e.g., the quantity, frequency, intensity, and/or other characteristics of) the stimulation provided to subject 12, and/or other sensors. Although sensor 18 is illustrated at a single location near subject 12, this is not intended to be limiting. Sensor 18 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), coupled with a bed and/or other furniture where subject 12 is sleeping, and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, user interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical user interfaces configured to facilitate user interaction with system 10.

As shown in FIG. 1, processor 20 is configured to execute one or more computer program components. The computer program components may comprise software programs and/or algorithms coded and/or otherwise embedded in processor 20, for example. The one or more computer program components may comprise one or more of a therapy component 30, an age matched reference component 32, a slow wave activity metric component 34, a stimulation quality metric component 36, a sleep architecture metric component 38, a combination component 40, an output component 42, and/or other components. Processor 20 may be configured to execute components 30, 32, 34, 36, 38, 40, and/or 42 by software; hardware; firmware; some combination of software, hardware, and/or firmware; and/or other mechanisms for configuring processing capabilities on processor 20.

It should be appreciated that although components 30, 32, 34, 36, 38, 40, and 42 are illustrated in FIG. 1 as being co-located within a single processing unit, in embodiments in which processor 20 comprises multiple processing units, one or more of components 30, 32, 34, 36, 38, 40, and/or 42 may be located remotely from the other components. The description of the functionality provided by the different components 30, 32, 34, 36, 38, 40, and/or 42 described below is for illustrative purposes, and is not intended to be limiting, as any of components 30, 32, 34, 36, 38, 40, and/or 42 may provide more or less functionality than is described. For example, one or more of components 30, 32, 34, 36, 38, 40, and/or 42 may be eliminated, and some or all of its functionality may be provided by other components 30, 32, 34, 36, 38, 40, and/or 42. As another example, processor 20 may be configured to execute one or more additional components that may perform some or all of the functionality attributed below to one of components 30, 32, 34, 36, 38, 40, and/or 42.

Therapy component 30 is configured to control one or more stimulators 16 to provide stimulation to subject 12 during sleep sessions. The one or more stimulators 16 are controlled to provide stimulation according to a predetermined therapy regime. Sleep slow waves can be enhanced through (e.g. peripheral auditory, magnetic, electrical, and/or other) stimulation delivered in NREM sleep. Enhancing sleep slow waves increases the restorative value of sleep. Therapy component 30 monitors the brain activity of subject 12 based on the output signals of sensors 18 (e.g., based on an EEG) and/or other information during sleep sessions and controls the delivery of stimulation (e.g., auditory and/or other stimulation) by stimulator 16 to control slow wave activity in subject 12. In some embodiments, therapy component 30 (and/or or more of the other processor components described below) performs one or more operations similar to and/or the same as the operations described in U.S. patent application Ser. No. 14/784,782 (entitled "System and Method for Sleep Session Management Based on Slow Wave Sleep Activity in a Subject"), Ser. No. 14/783,114 (entitled "System and Method for Enhancing Sleep Slow Wave Activity Based on Cardiac Activity"), Ser. No. 14/784,746 (entitled "Adjustment of Sensory Stimulation Intensity to Enhance Sleep Slow Wave Activity"), Ser. No. 15/101,008 (entitled "System and Method for Determining Sleep Stage Based on Sleep Cycle"), and/or Ser. No. 15/100,435 (entitled "System and Method for Facilitating Sleep Stage Transitions"), which are all individually incorporated by reference in their entireties.

Figure 2:
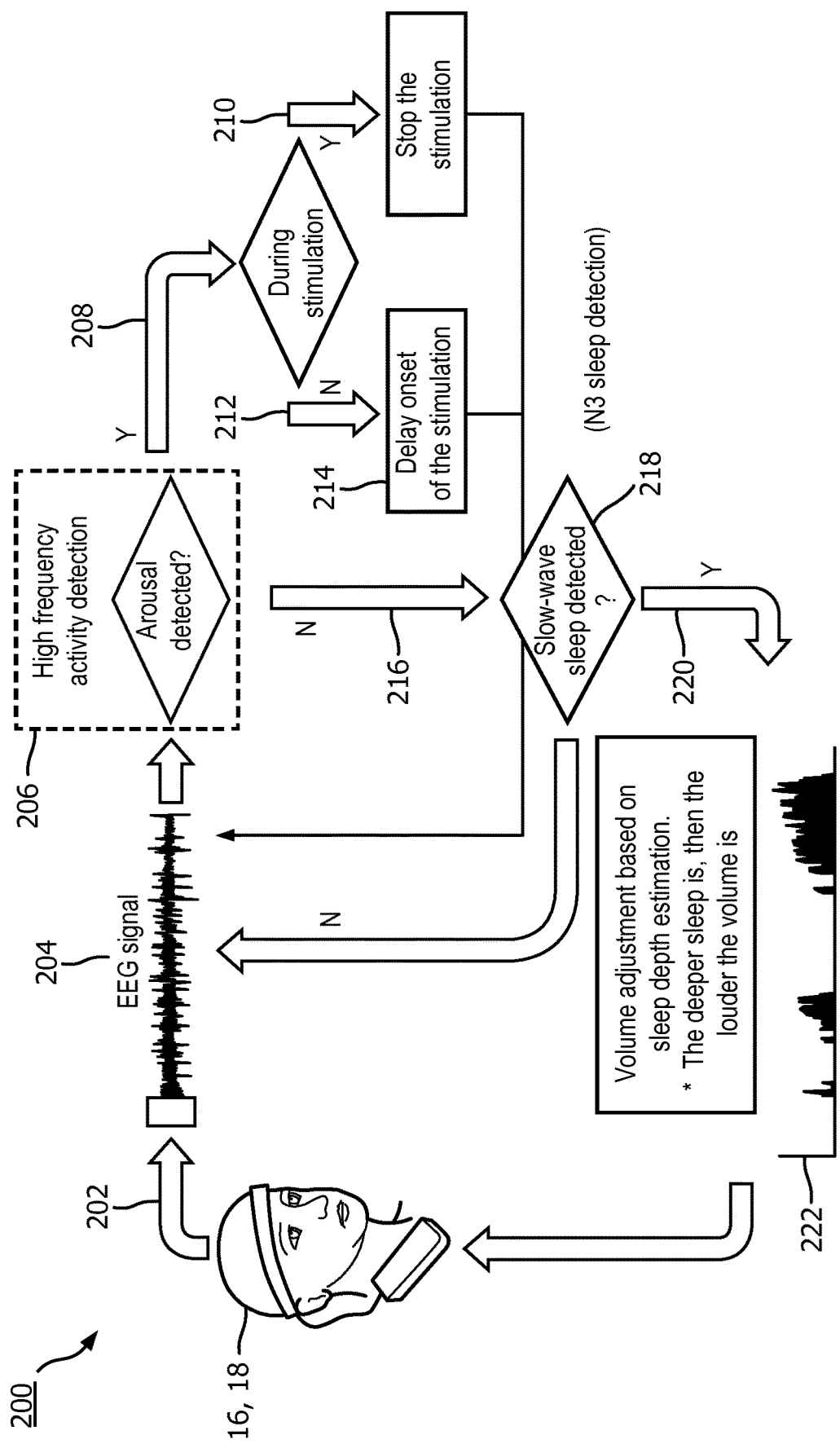
FIG. 2 illustrates examples of the operations performed by a therapy component of the system.

An example illustration of the operations 200 performed by therapy component 30 (shown in FIG. 1) is shown in FIG. 2. As shown in FIG. 2, EEG electrodes (e.g., sensors 18) generate 202 an EEG signal 204. The presence of EEG patterns (high power in the alpha 8-12 Hz and/or beta 15-30 Hz bands) indicative of (micro) arousals is evaluated 206 by therapy component 30 (FIG. 1). If arousal-like activity is detected 208 in the EEG during stimulation therapy component 30 controls stimulator 16 to stop 210 the stimulation. If the arousal-like activity is detected 212 outside the stimulation period, the onset of the next stimulation is delayed 214. If no arousal-like activity is detected 216, then therapy component 30 attempts to detect 218 deep sleep based on the power in the slow wave activity band (0.5 to 4 Hz), the temporal density of detected slow-waves, and/or other information. Responsive to detection of sufficiently deep sleep 220, therapy component 30 is configured to control stimulator 16 such that auditory (as in the example shown in FIG. 2 but this is not intended to be limiting) stimulation is delivered 222. Therapy component 30 is configured such that the volume (for example) of the auditory (for example) stimulation is modulated by a real time EEG based estimation of sleep depth that considers the sum of power ratios: delta power/alpha power+delta power/beta power. Consequently, the deeper sleep is, the louder the volume of the stimulation becomes.

Returning to FIG. 1, age matched reference component 32 is configured to obtain age matched reference information for subject 12. The age matched reference information for subject 12 indicates information related to reference amounts of cumulative slow wave activity during sleep sessions, reference levels of stimulation provided during sleep sessions, reference levels of sleep quality during sleep sessions, and/or other information for a population of subjects similar in age to subject 12. The age matched reference information comprises statistical distributions of various parameters related to slow wave activity, stimulation quality, sleep architecture, and/or other information across populations of one or more ages. In some embodiments, the statistical distributions include averages, standard deviations, maximums, minimums, ranges, changes in parameters over time, summations, quantiles (e.g., $50^{th}$ percent quantile and/or median value, etc.), and/or other statistical distributions. In some embodiments, the various parameters include cumulative slow wave activity (CSWA) during a sleep session, detected NREM sleep duration, average stimulation intensity (e.g., volume), maximum stimulation intensity (e.g., volume), minimum stimulation intensity (e.g., volume), a total quantity of individual stimulations (e.g., tones), a number of stimulations (e.g., tones) with a given intensity (e.g., volume), a stimulation density (e.g., a number of tones per given amount of time), TST, WASO, SOL, a quantity of arousals, count of slow waves, amplitude of slow waves, duration of sleep stages, count of spindles, frequency of spindles, and/or other parameters.

In some embodiments, the age matched reference information may comprise reference information for two, three, four, five, or more age ranges. By way of a non-limiting example, the age matched reference information may comprise sets of reference information for those under 20 years old, 20-30 year olds, 30-40 year olds, 40-60 year olds, and/or those over 60 years old.

In some embodiments, the age matched reference information for the different age groups is determined by age matched reference component 32 based on information from prior sleep sessions for subjects of various ages who have used system 10 and/or similar systems. In some embodiments, age matched reference component 32 may be configured to facilitate experimental determination of the age matched reference information for the different age groups. In some embodiments, facilitating experimental determination of the age matched reference information may include controlling stimulators 16, sensors 18, and/or other components of system 10 to stimulate (or not stimulate as in sham sessions) subjects of various ages and genders (e.g., 19 subjects, four female, fifteen male, ranging in age from 25 to 54 years old in one example experiment) over multiple sleep sessions (e.g., 180 sleep session recordings), record the information in the output signals from sensors 18, and determine one or more of the statistical distributions for one or more of the parameters described above.

In some embodiments, age matched reference component 32 is configured to obtain the age matched reference information from literature and/or other databases (e.g., that are part of external resources 26). In some embodiments, system 10 is configured such that the age matched reference information for the different age groups is stored in a database that is part of electronic storage 22, external resources 26, and/or other components of system 10, for example. In some embodiments, age matched reference component 32 is configured to update values of the statistical distributions for the various parameters. Age matched reference component 32 may update the values responsive to facilitating further experimental determination of additional age matched reference information, obtaining additional age matched reference information that has become available in the literature and/or other databases included in external resources 26, facilitating entry and/or selection of updated information by subject 12 and/or other users (e.g., doctors, nurses, caregivers, family members, researchers, etc.) via user interface 24, and/or perform other updates.

In some embodiments, age matched reference component 32 is configured to facilitate entry and/or selection of the age of subject 12 via user interface 24 and/or other components of system 10 and compare the entered and/or selected age of subject 12 to the age ranges described above and/or other age ranges. Based on the comparison, age matched reference component 32 determines which age range corresponds to the age of subject 12, and obtains the appropriate age matched reference information from electronic storage 22 and/or other sources. The obtained age matched reference information that corresponds to the age of subject 12 is used (e.g., by slow wave activity metric component 34, stimulation quality metric component 36, sleep architecture metric component 38, and/or other components) to determine the metrics as described below.

Slow wave activity metric component 34 is configured to determine a slow wave activity metric. The slow wave activity metric is indicative of a cumulative amount of slow wave activity in subject 12 during the sleep session. The slow wave activity metric is determined based on the output signals, the stimulation provided to subject 12, the age matched reference information, and/or other information. In some embodiments, the slow wave activity metric is determined based on a cumulative slow wave activity factor (CSWA) and an NREM duration factor. In some embodiments, the slow wave activity metric is determined based on Equation 1.

Slow Wave Activity Metric=100×CSWA Factor×
NREM duration factor      (1)

In some embodiments, the cumulative slow wave activity and NREM factors are both determined based on the output signals, the age matched reference information, and/or other information.

In some embodiments, the CSWA factor is and/or is determined based on cumulative EEG power in a 0.5 to 4 Hz band across detected NREM epochs during the sleep session determined automatically by slow wave activity metric component 34. In some embodiments, to ensure appropriate frequency resolution and/or for other reasons, slow wave activity metric component 34 is configured such that 6-second long epochs are considered. Responsive to therapy component 30 and/or other components of system 10 using epochs of different durations to determine sleep stages in subject 12, slow wave activity metric component 34 may be configured such that an extra step of down-sampling (e.g., if the sleep staging epochs are shorter) and/or up-sampling (e.g., if the sleep staging epochs are longer) is applied to obtain 6-second long epochs.

Figure 3:
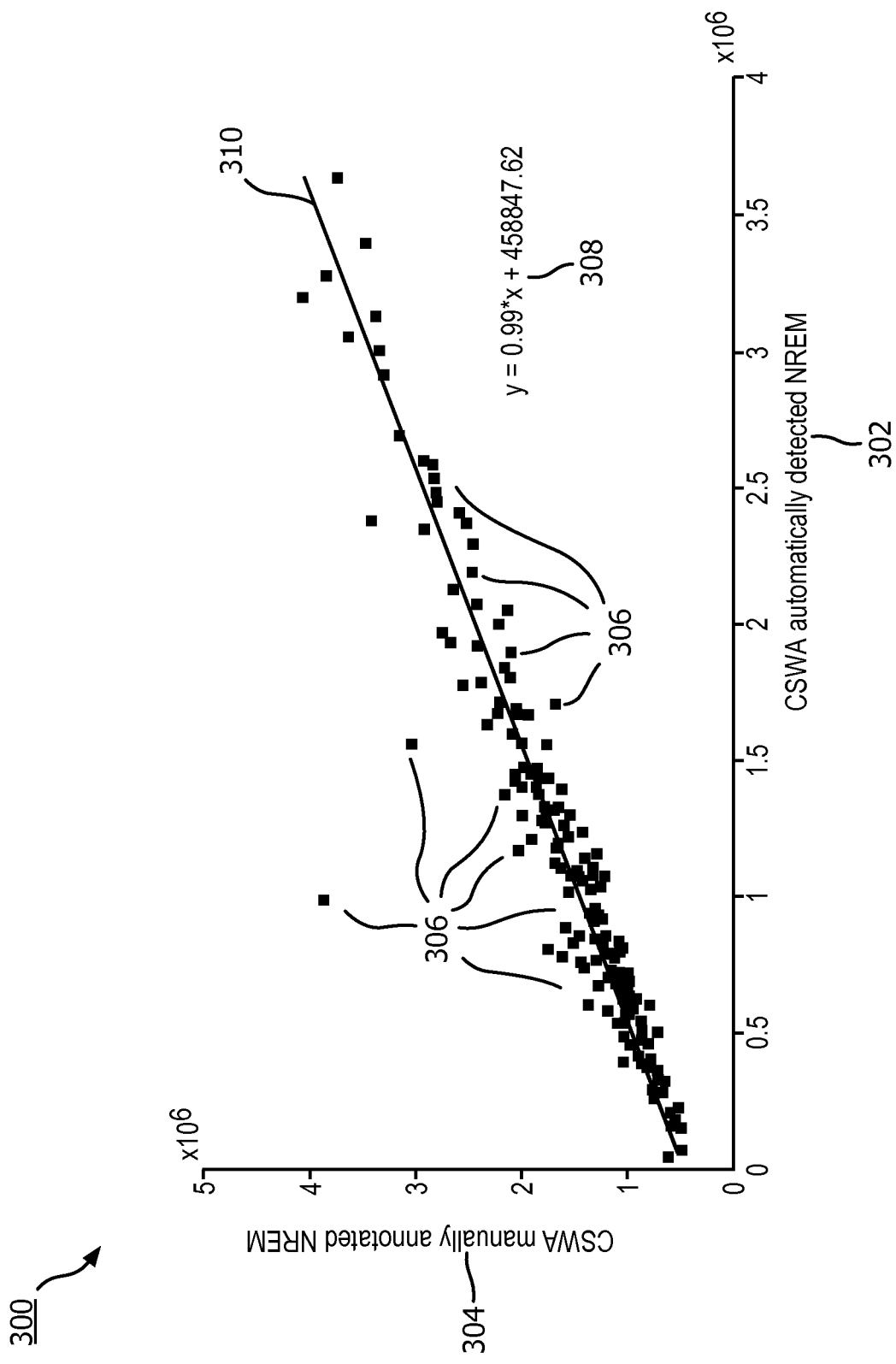
FIG. 3 illustrates correlation between automatically determined and manually determined cumulative slow wave activity in the subject.

In some embodiments, slow wave activity metric component 34 is configured such that the automatic determination of the CSWA factor by slow wave activity metric component 34 correlates with cumulative slow wave activity determined based on manually annotated NREM epochs. This is illustrated in FIG. 3. FIG. 3 is a plot 300 of CSWA 302 determined based on automatically detected NREM duration versus CSWA 304 determined based on manually annotated NREM duration for CSWA from the same sleep sessions 306. As shown in FIG. 3, the correlation 308 of the linear data fit 310 is near 1.0.

Figure 4:
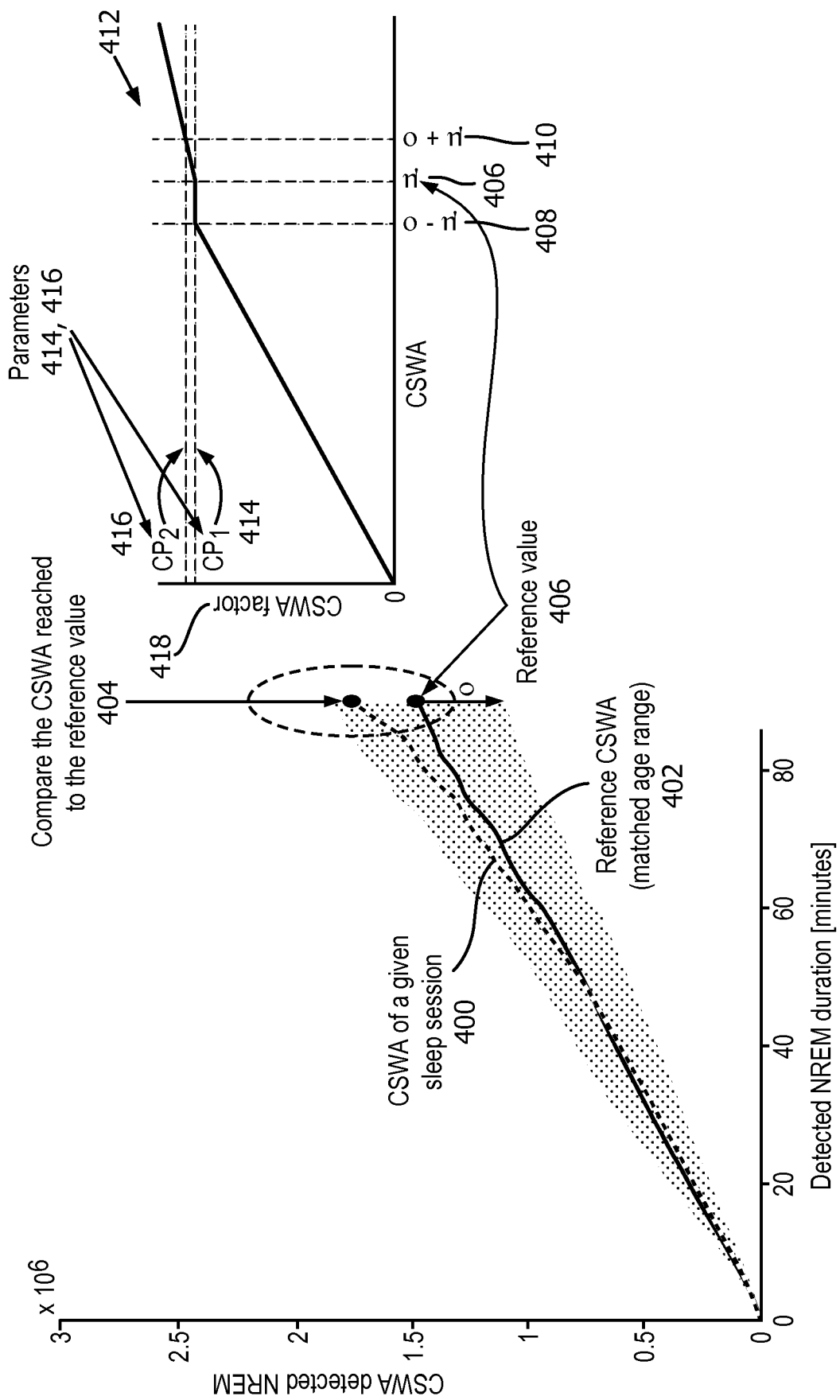
FIG. 4 illustrates determination of a cumulative slow wave activity factor.

FIG. 4 further illustrates determination of the CSWA factor. Given the CSWA of a given sleep session 400 determined by slow wave activity metric component 34 based on the output signals for subject 12 (FIG. 1) for a given sleep session, the CSWA factor is determined using reference CSWA information 402 for the age range to which subject 12 belongs. Slow wave activity metric component 34 is configured to compare the CSWA reached 404 by subject 12 in the sleep session to a corresponding age matched reference value 406 (represented by $\mu$ in FIG. 7) of CSWA. The age matched reference value 406 and standard deviations ($\sigma$) and 408 ($\sigma$-$\mu$), 410 ($\sigma$+$\mu$) around reference value 406 are shown the CSWA factor determination plot 412 in FIG. 4. The CSWA factor is determined based on plot 412 where $CP_1$ and $CP_2$ are configurable parameters 414 and 416. In some embodiments, slow wave activity metric component 34 (FIG. 1) is configured such that $CP_1$ and/or $CP_2$ are determined at manufacture, entered and/or selected via user interface 24 (FIG. 1), determined based on previous sleep sessions of subject 12 (FIG. 1) and/or other subjects, and/or determined in other ways.

In this example (and the examples described below for the slow wave activity metric and the other metrics), the indicator determined by system 10 is a numerical score, the metrics described herein are numerical sub-scores that are weighted and combined to determine the indicator, and the CSWA factor is a numerical sub-score of the slow wave activity metric. As shown in FIG. 4, the parameters $CP_1$ and $CP_2$ were set to 1 and 1.1 respectively. This means that in this example, if CSWA 404 in subject 12 is more than one standard deviation less 408 than the age matched average amount of CSWA 406, the CSWA factor 418 has a value that linearly decreases from one to zero depending on the amount of CSWA. If CSWA 404 is more than one standard deviation above 410 the age matched average amount of CSWA 406, CSWA factor 418 increases linearly from 1.1. Between CSWA 408 and CSWA 410, CSWA factor 418 is constant at 1 until CSWA 406 and then linearly increases from 1 to 1.1 until CSWA 410.

In some embodiments, slow wave activity metric component 34 (FIG. 1) is configured such that the NREM duration factor is determined based on Equation 2.

$$NREM\ dur.\ factor = \max\left\{0,\ \min\left\{\phi_1,\ \frac{\phi_1}{\mu_{dur} - \sigma_{dur}} d_{NREM}\right\}\right\} + \max\left\{0,\ \frac{\phi_2 - \phi_1}{\sigma_{dur}}(d_{NREM} - \mu_{dur})\right\} \quad (2)$$

where $\mu_{dur}$ and $\sigma_{dur}$ are the mean and standard deviation of the NREM detected duration for the corresponding age matched age range for subject 12 (FIG. 1), $d_{NREM}$ is the duration of NREM sleep detected for subject 12 during the sleep session by slow wave activity component 34 based on the output signals, and $\phi_1$ and $\phi_2$ are configurable parameters (like $CP_1$ and $CP_2$) that determine the value of the NREM duration factor based on the NREM duration determined for subject 12. In some embodiments, slow wave activity metric component 34 (FIG. 1) is configured such that $\phi_1$ and/or $\phi_2$ are determined at manufacture, entered and/or selected via user interface 24 (FIG. 1), determined based on previous sleep sessions of subject 12 (FIG. 1) and/or other subjects, and/or determined in other ways.

Figure 5:
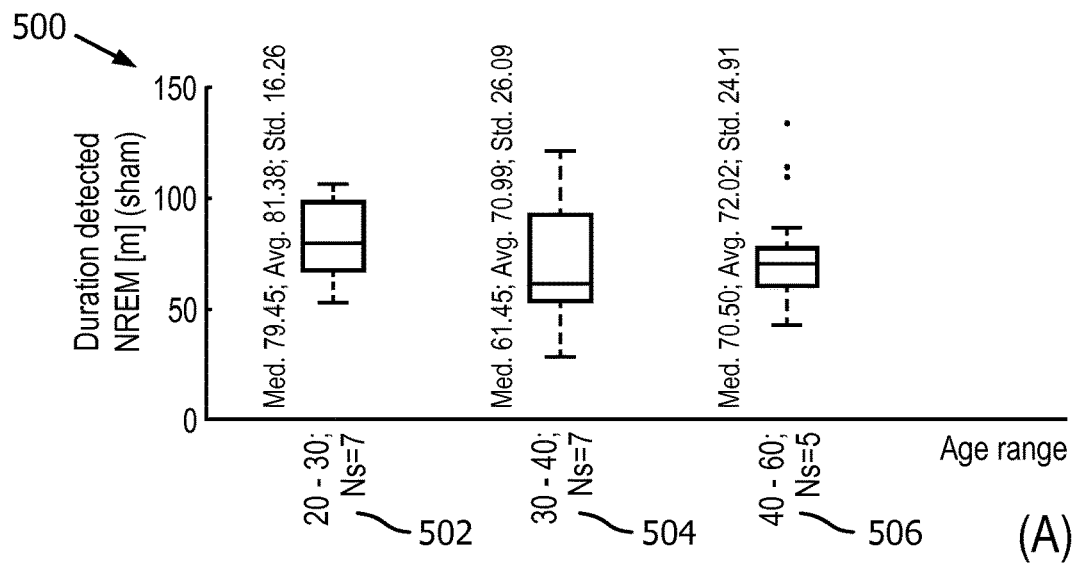
FIG. 5 illustrates determination of an NREM duration factor.
Figure 5:
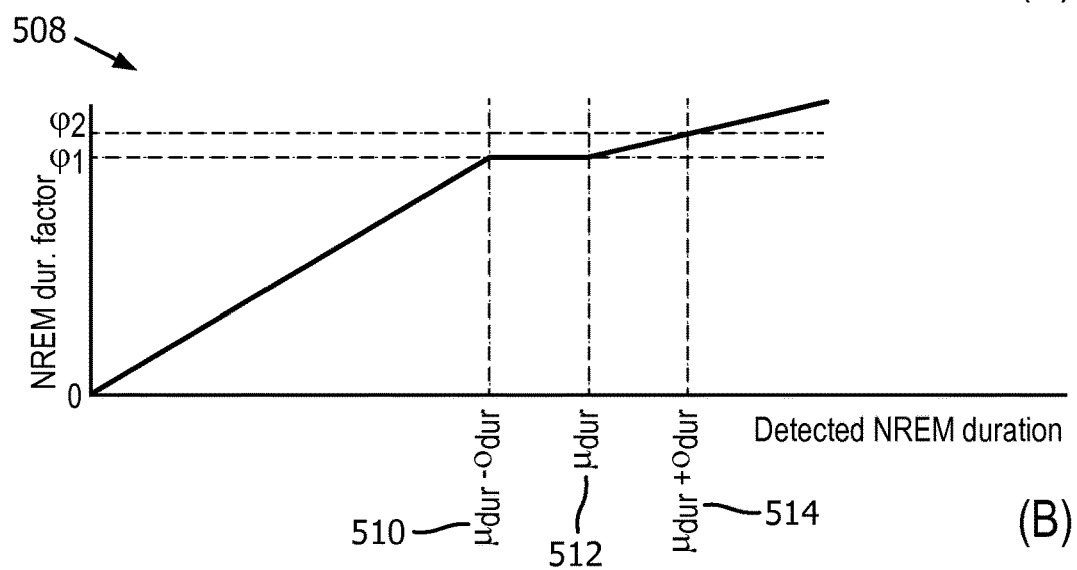
Figure 5:
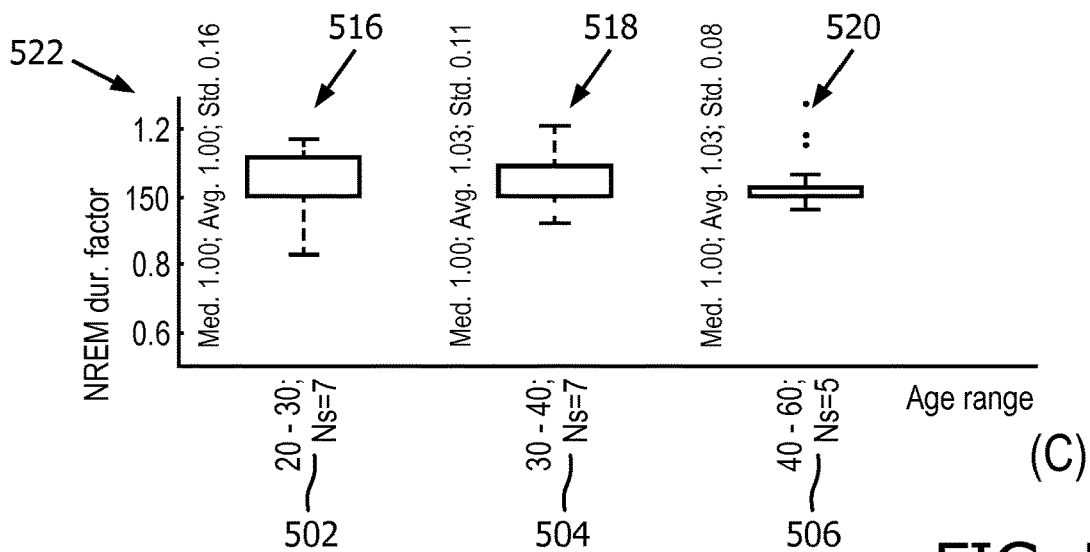

FIG. 5 illustrates determination of the NREM duration factor. FIG. 5(a) illustrates example age matched reference NREM duration information 500 for three different age ranges 502, 504, 506. As shown in FIG. 5(b) (similar to plot 412 in FIG. 4), the NREM duration factor 508 is equal to $\phi_1$ if $d_{NREM}$ is between $\mu_{dur}-\sigma_{dur}$ 510 and $\mu_{dur}$ 512, linearly decreases for values of $d_{NREM}$ lower than $\mu_{dur}-\sigma_{dur}$ 510, and progressively increases for values of $d_{NREM}$ higher than $\mu_{dur}$ 512, with a value of $\phi_2 > \phi_1$ for $d_{NREM}=\mu_{dur}+\sigma_{dur}$ 514. In this example, $\phi_1$ and $\phi_2$ are 1 and 1.1 respectively (this is not intended to be limiting). FIG. 5(b) illustrates ranges 516, 518, 520 of example NREM duration factors 522 for the three different age ranges 502, 504, and 506.

Figure 6:
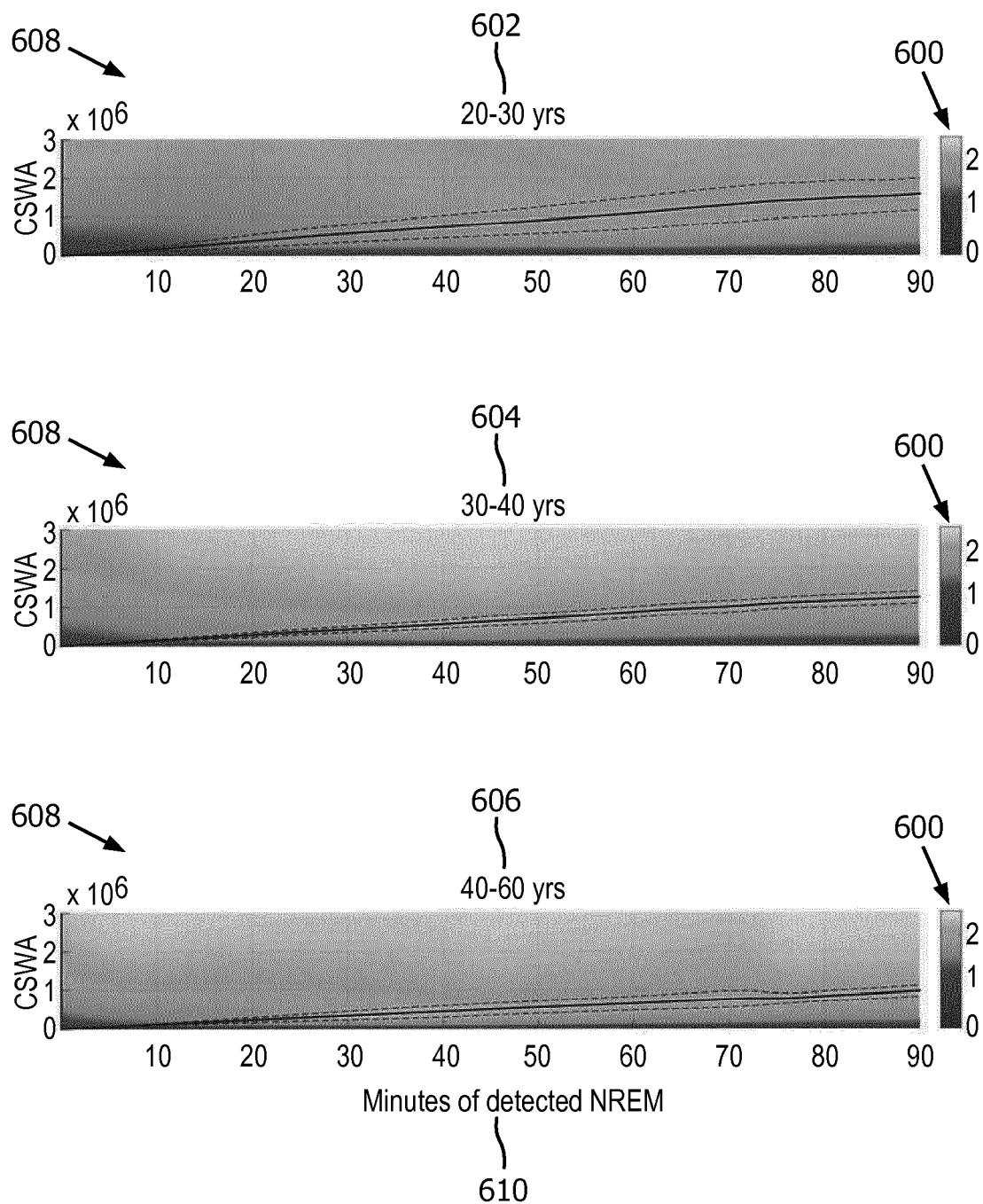
FIG. 6 illustrates determination of a slow wave activity metric.

As described above, slow wave activity metric component 34 (FIG. 1) is configured to determine the slow wave activity metric based on Equation 1 (e.g., 100×NREM duration factor×CSWA factor). FIG. 6 illustrates determination of the slow wave activity metric 600 (shown as a log shaded color scale) for three example age ranges 602, 604, 606 that may correspond to the age of subject 12 (FIG. 1). The value of slow wave activity metric 600 depends on the age range. For the individual age ranges 602, 604, 606 shown in FIG. 6, age matched reference CSWA 608 versus detected NREM 610 and standard deviation are represented with solid and dashed lines respectively.

Returning to FIG. 1, stimulation quality metric component 36 is configured to determine a stimulation quality metric. The stimulation quality metric is indicative of how well the stimulation enhances slow wave activity in subject 12 during the sleep session. The stimulation quality metric is determined based on the output signals, the stimulation provided to subject 12, the age matched reference information, and/or other information. In some embodiments, the stimulation quality metric is and/or is related to one or more of the average stimulation intensity (e.g., volume), maximum stimulation intensity (e.g., volume), minimum stimulation intensity (e.g., volume), a total quantity of individual stimulations (e.g., tones), a number of stimulations (e.g., tones) with a given intensity (e.g., volume), a stimulation density (e.g., a number of tones per given amount of time), and/or other characteristics of the stimulation.

In some embodiments, the stimulation quality metric is and/or is related to a characteristic that correlates with slow wave activity enhancement in subject 12. In some embodiments, stimulation quality metric component 36 is configured to determine which characteristic of the stimulation correlates with slow wave activity enhancement by determining a linear regression model to analyze the dependency of slow wave activity in subject 12 on the various characteristics (e.g., the characteristics listed above). By way of a non limiting example, stimulation quality metric component 36 may determine a linear regression model using one or more of average volume across all tones (<V>), maximum volume reached ($V_M$), minimum volume ($V_m$), sum of volume across all tones (total "acoustic energy") as shown in Equation 3:

$$\left(\sum_{tone\_i} Vi\right), \quad (3)$$

number of tones with volume ≤55 dB ($\#V_{\leq 55}$), number of tones with volumes: 55<$V_i$≤60 dB ($\#V_{[55,60]}$), number of tones with volumes: 60<$V_i$≤65 dB ($\#V_{[60,65]}$), number of tones with volumes: 65<$V_i$≤70 dB ($\#V_{[65,70]}$), number of tones with volumes: 70<$V_i$≤75 dB ($\#V_{[70,75]}$), and/or density of tones: #tones per detected N3 duration ($\rho_{tones}$). In some embodiments, stimulation quality metric component 36 is configured such that the linear model in Equation 4 (below), has weight coefficients "$\beta_i$" that are estimated based on standard algorithms and indicate the relative importance of the associated stimulation property (e.g., provided that the terms in Equation (3) are z-scored).

$$CSWA = \beta_1 <V> + \beta_2 V_M + \beta_3 V_m + \beta_4 \Sigma_{tone_i} V_i + \beta_5 \#V_{\leq 55} + \beta_6 \#V_{[55,60]} + \beta_7 \#V_{[60,65]} + \beta_8 \#V_{[65,70]} + \beta_9 \#V_{[70,75]} + \beta_{10} \rho_{tone} \quad (4)$$

In this example, the three most statistically significant linear model coefficients are: $\#V_{\leq 55}$ with $\beta_5 = 0.48$ and significance value p=7.4 e-10, $\#V_{[55,60]}$ with $\beta_6 = 0.49$ and significance value p=1.9 e-6, and $\rho_{tones}$ with $\beta_{10} = -1.25$ and significance value p=3.9 e-15. This indicates that the stimulation property that has most positive (correlation) influence on CSWA is the number of tones with volume lower or equal than 60 dB. The statistically significant correlation between the number of tones with volume ≤60 dB and CSWA is shown in FIG. 7.

Figure 7:
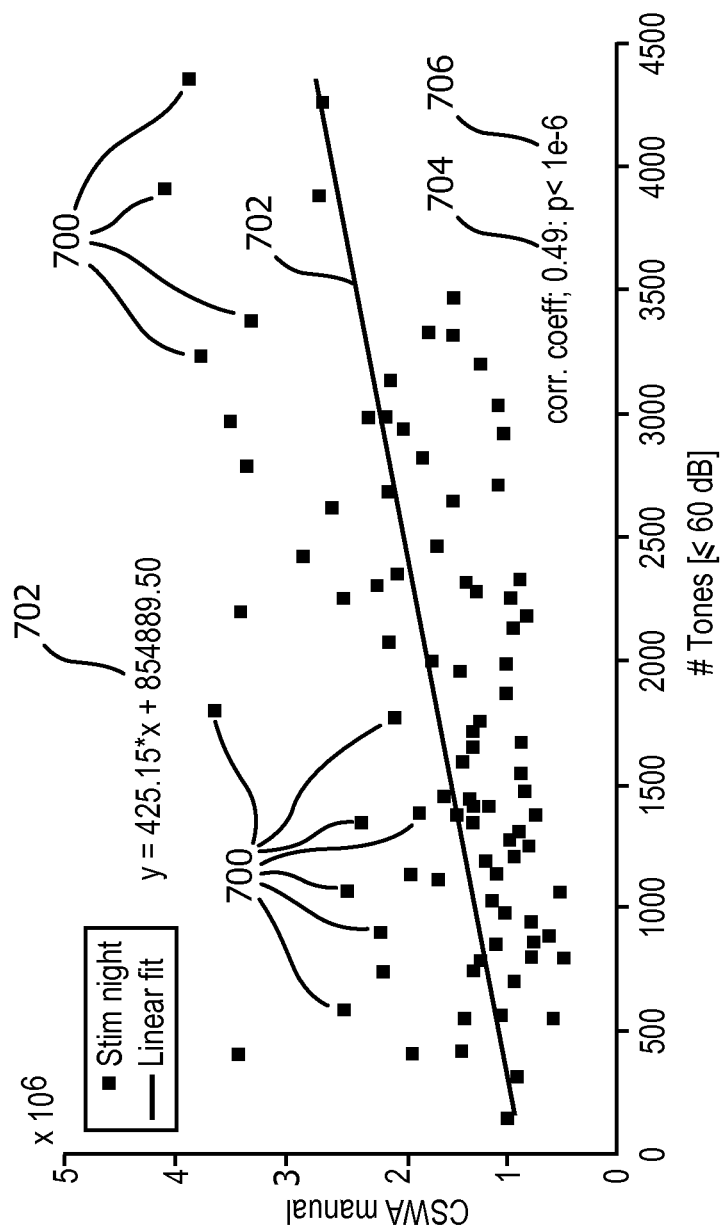
FIG. 7 illustrates correlation between a number of stimulation tones during a sleep session and cumulative slow wave activity.

FIG. 7 illustrates various data points 700 for multiple nights of sleep (sleep sessions) where a subject received stimulation, a linear fit 702 to data points 700, a correlation coefficient 704 close to 0.5 and a p value 706 that is less than 1 e-6. Thus, the quality of the stimulation is quantified in this example embodiment using the number of tones at volume lower than or equal to 60 dB. This example is not intended to be limiting and should not be considered to exclude the use of other stimulation characteristics and/or combinations thereof to quantify the stimulation quality.

Figure 8:
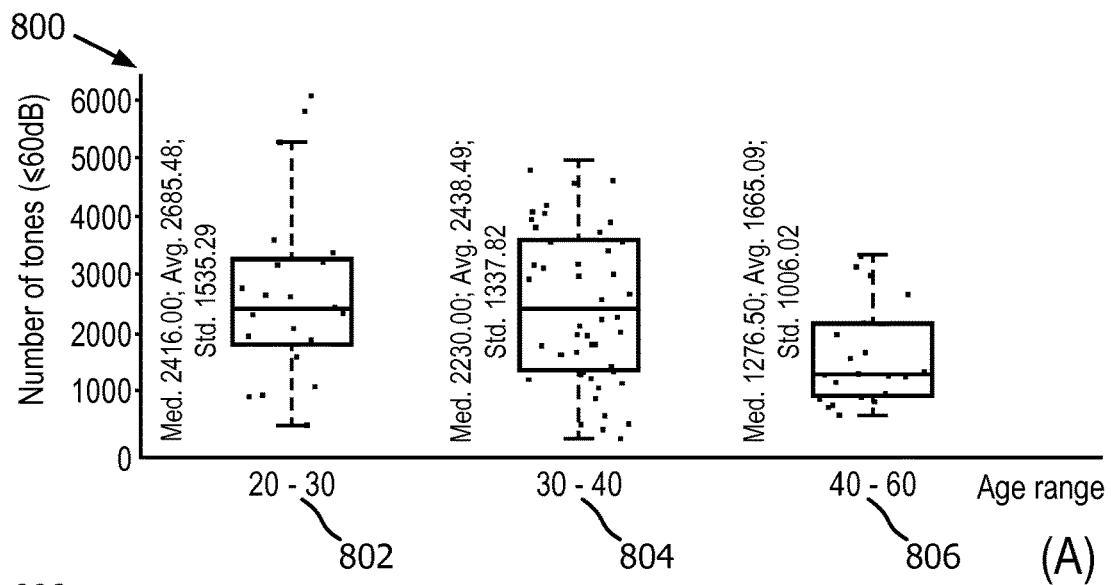
FIG. 8 illustrates determination of a stimulation quality metric.
Figure 8:
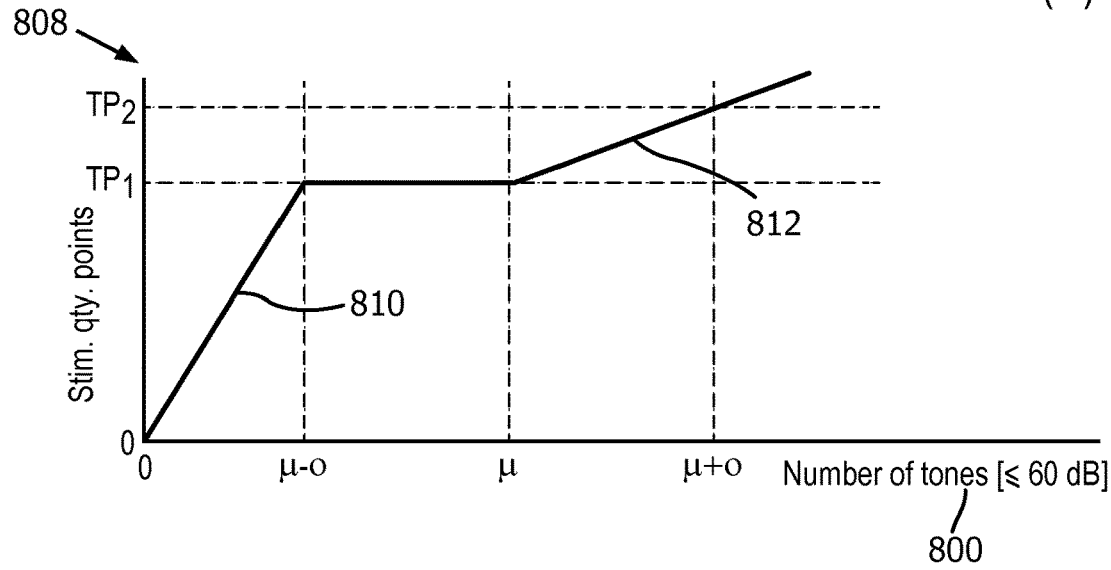
Figure 8:
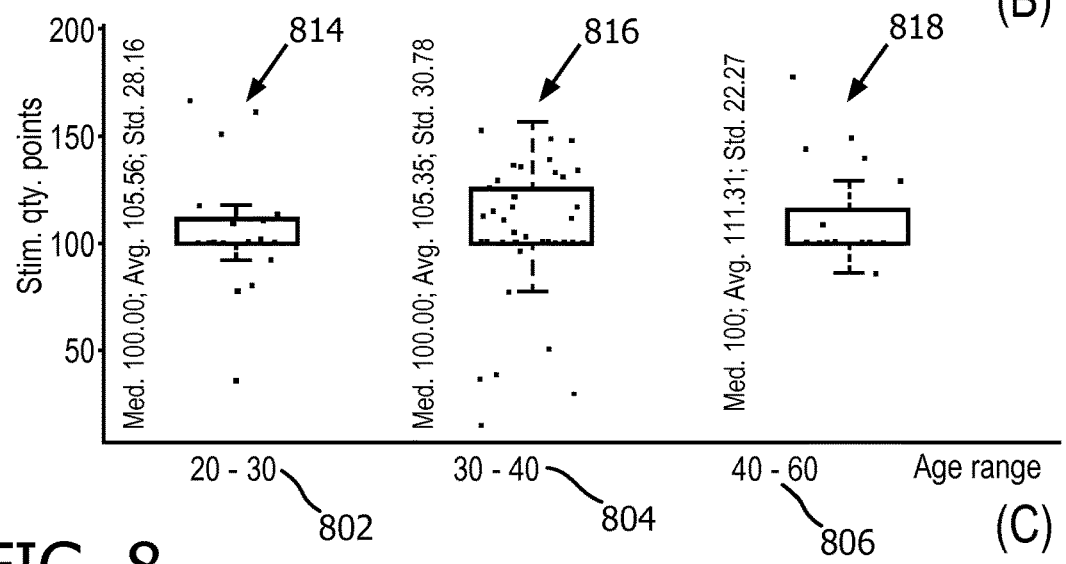

FIG. 8 illustrates determination of the stimulation quality metric based on the number of tones at volume lower than or equal to 60 dB. In some embodiments, stimulation quality metric component 36 (FIG. 1) is configured to analyze the number of tones at volume lower than 60 dB 800 for the age matched reference information. A distribution for three example age ranges 802, 804, 806 is shown in FIG. 8(a). The differences in the number of tones between age ranges results from the fact that the duration of deep sleep lowers with age. The mean ($\mu$) and standard deviation ($\sigma$) values per distribution (e.g., determined by stimulation quality metric component 36) are used by stimulation quality metric component 36 to determine a number of points (e.g., in the example embodiment where the indicator is a score as described above) associated with stimulation quality (stim. qty. points) according to Equation 5 (below) and/or FIG. 8(b).

$$stim.\ qty.\ points = \max\left\{0, \min\left\{TP_1, \frac{TP_1}{\mu - \sigma} N_t\right\}\right\} + \max\left\{0, \frac{TP_2 - TP_1}{\sigma}(N_t - \mu)\right\} \quad (5)$$

As shown in FIG. 8(b), $TP_1$ points 808 are given if the number of tones is between ($\mu-\sigma$) and $\mu$, and a proportional number of points 810 are given if the number of tones is lower than ($\mu-\sigma$). If more than $\mu$ tones are delivered, then the number of points 812 linearly increases with a value of $TP_2$ (>$TP_1$) when the number of tones is ($\mu+\sigma$).

In Equation 5, $N_t$ is the number of tones (volume ≤60 dB), and $\mu$ and $\sigma$ are the mean and standard deviation for the corresponding age range. The stimulation quality point distributions 814, 816, 818 using this model for (example) individual age ranges 802, 804, 806 are shown in FIG. 8(c)

(for the example $TP_1=100$ and $TP_2=130$). Because of the age normalization, the point distributions are similar across age ranges (in particular, for example, the medians are 100). $TP_1$ and/or $TP_2$ (like $\phi_1$ and $\phi_2$, and/or $CP_1$ and $CP_2$) are configurable parameters. In some embodiments, stimulation quality metric component 36 (FIG. 1) is configured such that $TP_1$ and/or $TP_2$ are determined at manufacture, entered and/or selected via user interface 24 (FIG. 1), determined based on previous sleep sessions of subject 12 (FIG. 1) and/or other subjects, and/or determined in other ways.

Returning to FIG. 1, sleep architecture metric component 38 is configured to determine a sleep architecture metric. The sleep architecture metric is indicative of a sleep quality for subject 12 during the sleep session. The sleep architecture metric is determined based on the output signals, the stimulation provided to subject 12, the age matched reference information, and/or other information. In some embodiments, the sleep architecture metric is determined based on the age matched reference information and one or more of a sleep onset latency value for subject 12, a wake after sleep onset value for subject 12, a total sleep time during the sleep session, a number of arousals during the sleep session, and/or other information. In some embodiments, the sleep onset latency value, the wake after sleep onset value, the total sleep time, and/or the number of arousals are determined based on the output signals and/or other information.

Figure 9:
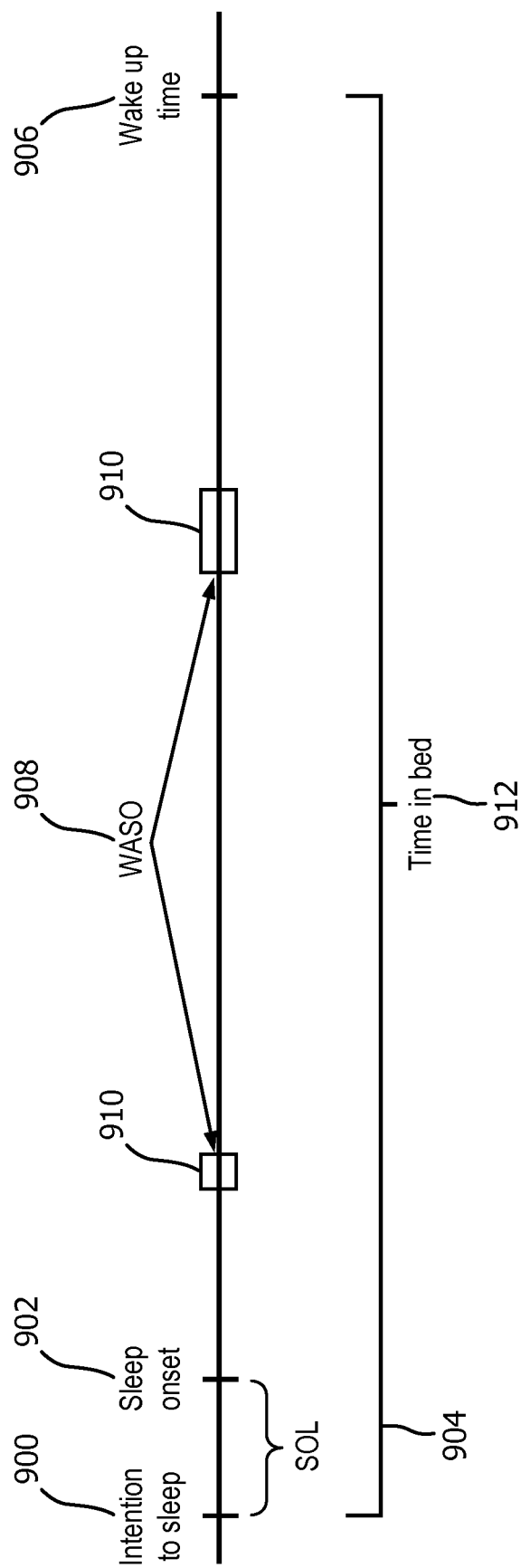
FIG. 9 illustrates sleep architecture parameters.

In some embodiments, sleep architecture metric component 38 is configured to determine sleep onset latency values, wake after sleep onset values, total sleep time, the number of arousals, and/or other sleep architecture parameters based on an automatically generated (e.g., by sleep architecture metric component 38 and/or other components of processor 20 based on the output signals from sensors 18 and/or other information) hypnogram. Examples of these and/or other sleep architecture parameters are illustrated in FIG. 9. For example, intention to sleep 900 comprises a first continuous 30 s (for example) long epoch of eyes closed before sleep onset (e.g., a first epoch where no eye blinks are present and, optionally for example, subject 12 (FIG. 1) shows an increase in the EEG alpha power). Sleep onset 902 comprises a first continuous 180 s (for example) long epoch of sleep. Sleep onset latency (SOL) 904 comprises a time elapsed between the detected intention to sleep 900 and the detected sleep onset 902. Wake up time 906 comprises an end of last epoch of sleep before the end of the sleep session. Wake after sleep onset (WASO) 908 comprises a duration of wake epochs between sleep onset and wake up events 910. Time in bed 912 comprises time elapsed between intention to sleep 900 and wake up time 906. Total sleep time (TST) (not shown in FIG. 9) comprises wake up time 906 minus sleep onset time 902, minus WASO 908. Arousals (not shown in FIG. 9) comprise a number of arousals per hour of sleep (e.g., and/or in some embodiments, longer than a predefined duration, e.g., 5 minutes).

Figure 10:
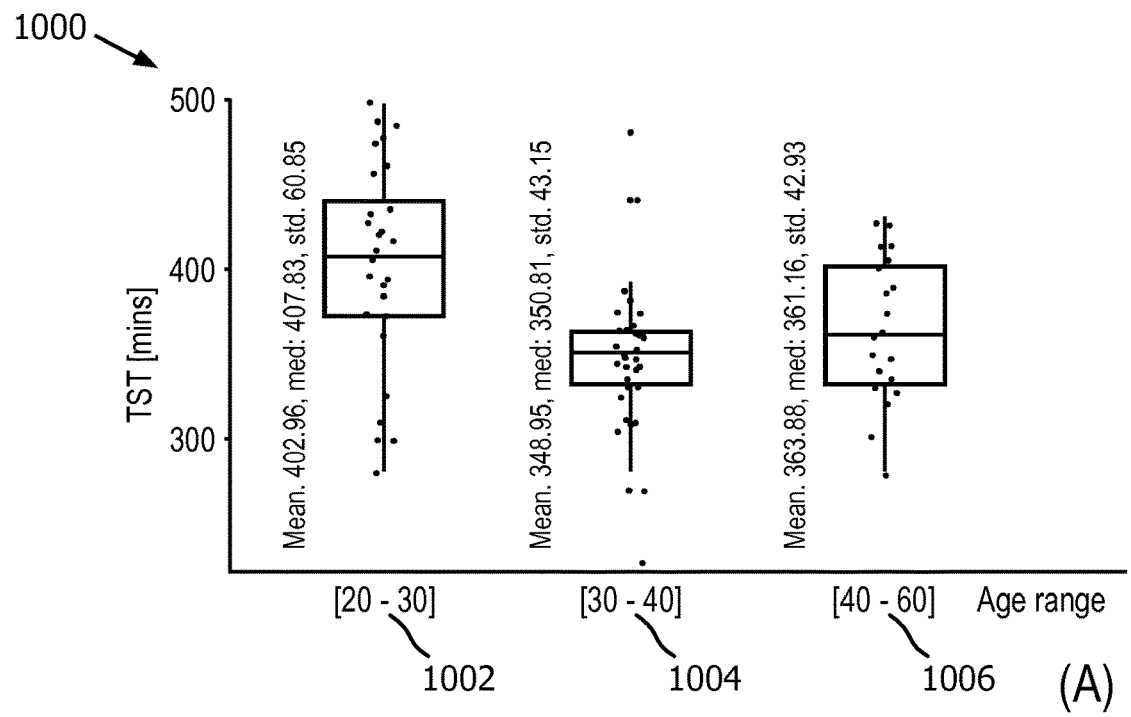
FIG. 10 illustrates determining total sleep time points.
Figure 10:
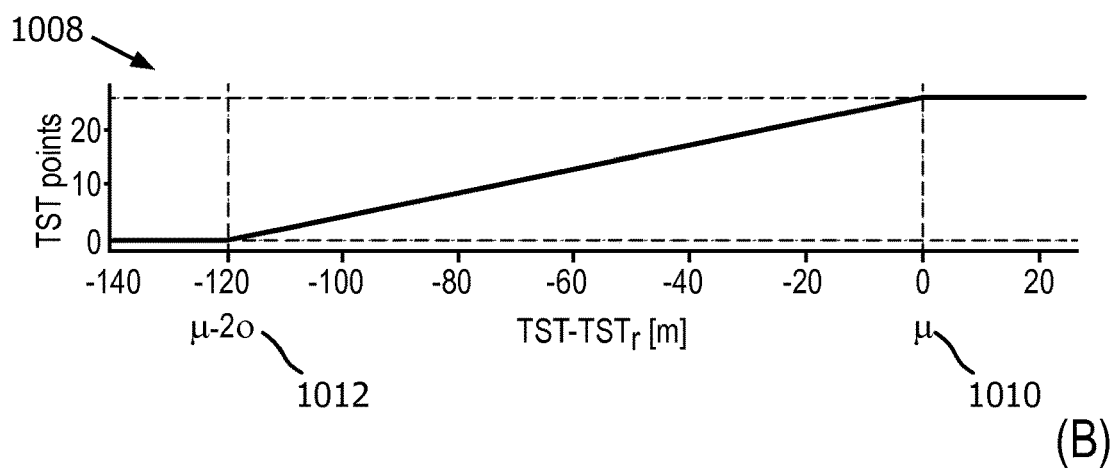
Figure 10:
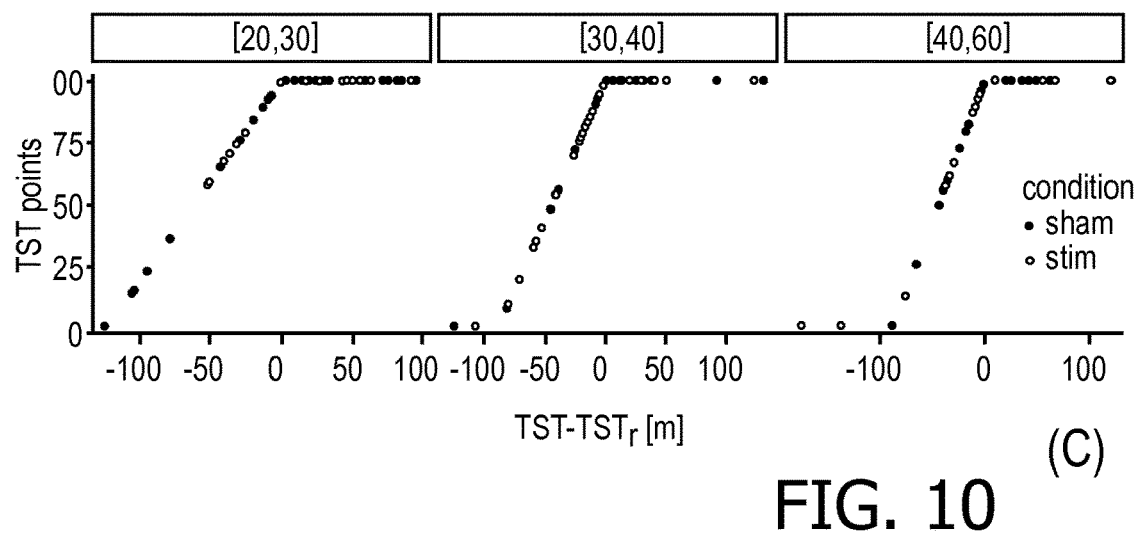

FIG. 10 illustrates determining total sleep time (TST) points (in this example where the indicator is a score) that contribute to the overall determination of the indicator as described herein. FIG. 10(a) illustrates TST distribution 1000 for three (for example) different age ranges 1002, 1004, 1006 in the age matched reference information. The mean ($\mu$) and standard deviation ($\sigma$) values (e.g., determined by sleep architecture metric component 38 and/or other components of processor 20) for individual age groups are used to determine the number of points associated with TST according to Equation 6 and FIG. 10(b).

$$TST \text{ points} = \min\left\{1, \max\left\{0, \frac{TST_i - \mu + 2*\sigma}{2*\sigma}\right\}\right\} * W_{TST} * 100 \quad (6)$$

As shown in FIG. 10(b), sleep architecture metric component 38 is configured such that $W_{TST}$ points 1008 are given if the TST matches the mean $\mu$ 1010. A linearly decreasing number of points are given if the TST is within 2 standard deviation of the age matched mean ($\mu-2*\sigma$) 1012. If the TST is below $\mu-2*\sigma$, then the number of points assigned is 0. This method rewards longer TST and penalizes short TST. In Equation 6, $TST_i$ is the TST for a given sleep session, and $\mu$ and $\sigma$ are the mean and standard deviation for the corresponding age range. The TST points using this model for the individual age range examples are show in FIG. 10(c).

Figure 11:
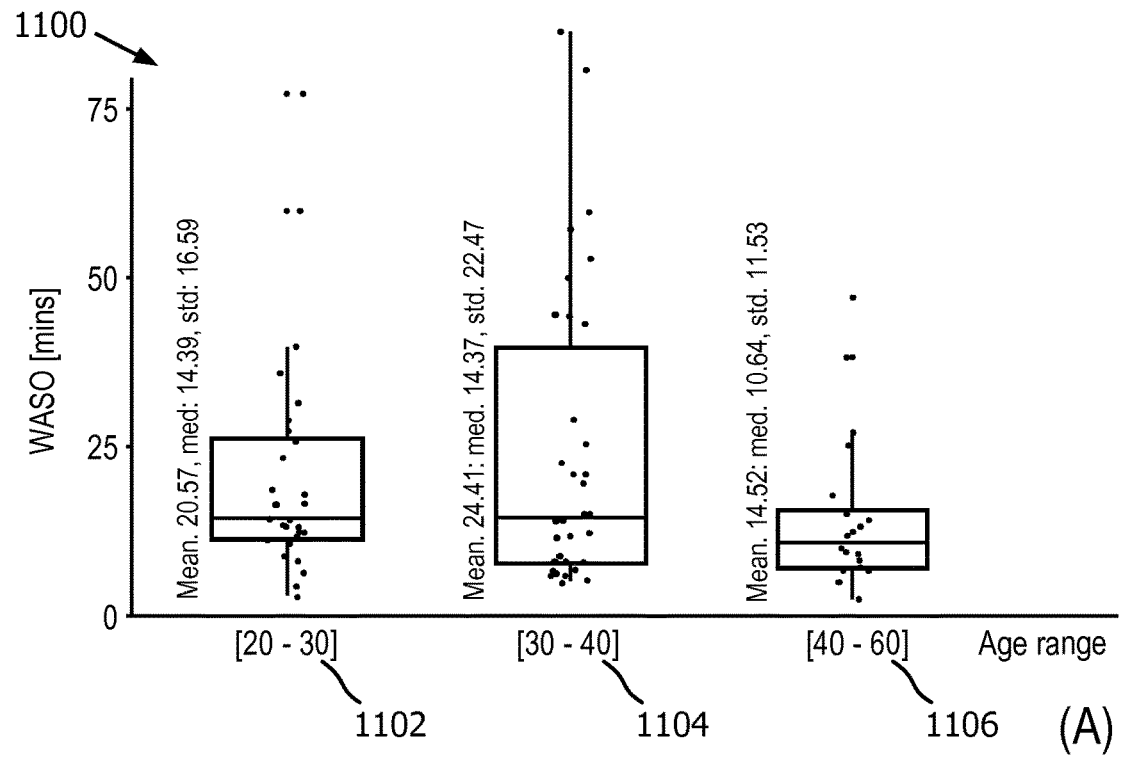
FIG. 11 illustrates determining wake after sleep onset points.
Figure 11:
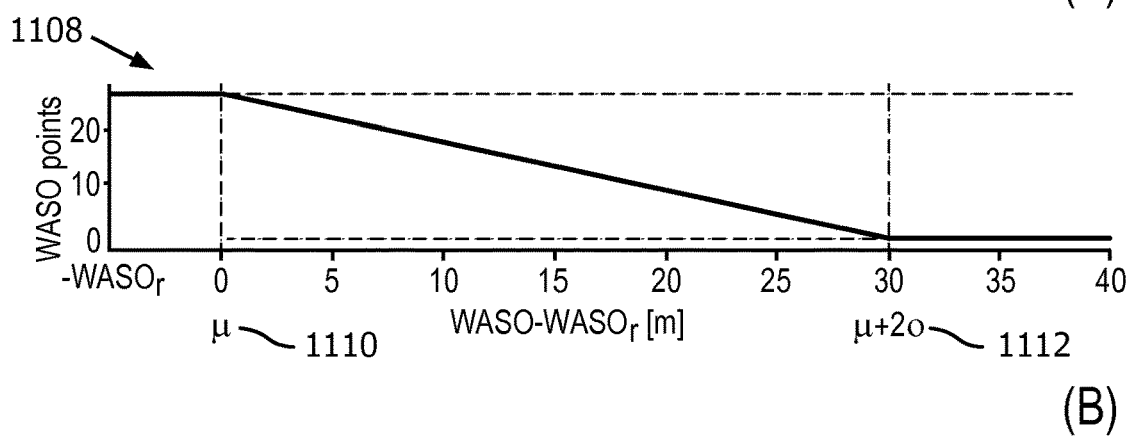
Figure 11:
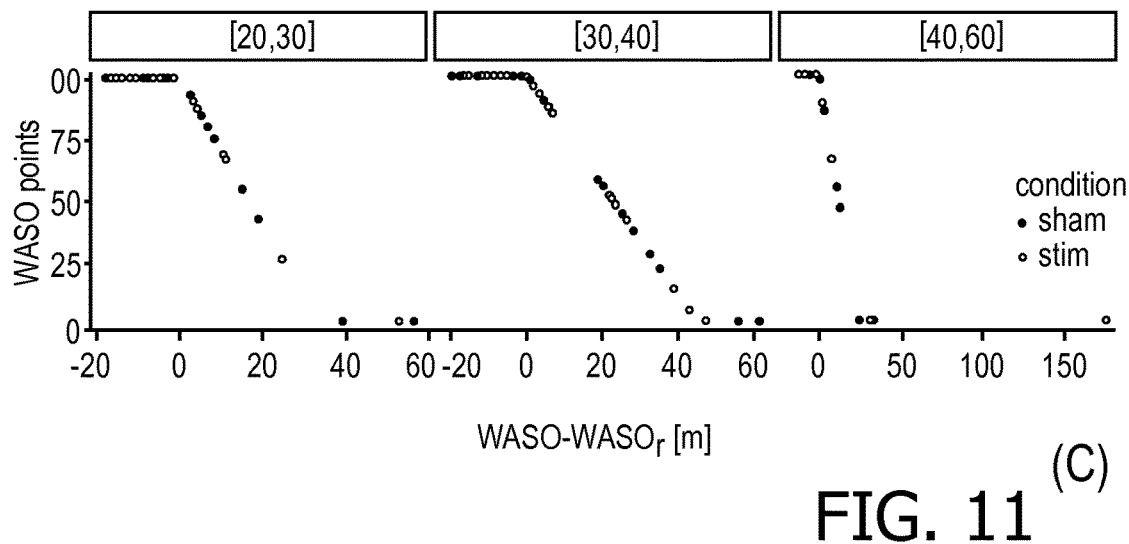

FIG. 11 illustrates determining WASO points (in this example where the indicator is a score) that contribute to the overall determination of the indicator as described herein. FIG. 11(a) illustrates WASO distribution 1100 for three (for example) different age ranges 1102, 1104, 1106 in the age matched reference information. The mean ($\mu$) and standard deviation ($\sigma$) values (e.g., determined by sleep architecture metric component 38 and/or other components of processor 20) for individual age groups are used to determine the number of points associated with WASO according to Equation 7 and FIG. 11(b).

$$WASO \text{ points} = \min\left\{1, \max\left\{0, \frac{\mu - WASO_i + 2*\sigma}{2*\sigma}\right\}\right\} * W_{WASO} * 100 \quad (7)$$

As shown in FIG. 11(b), sleep architecture metric component 38 is configured such that $W_{WASO}$ points 1108 are given if the WASO is at the age matched mean $\mu$ 1110. A linearly decreasing number of points are given if the WASO is within two standard deviations of the age matched mean ($\mu+2*\sigma$) 1112. If the WASO is above $\mu+2*\sigma$, then the number of points assigned is 0. This method penalizes long WASO. In Equation 7, $WASO_i$ is the WASO for a particular sleep session, and $\mu$ and $\sigma$ are the mean and standard deviation for the corresponding age range. The WASO points using this model for the individual example age ranges are show in FIG. 11(c).

Figure 12:
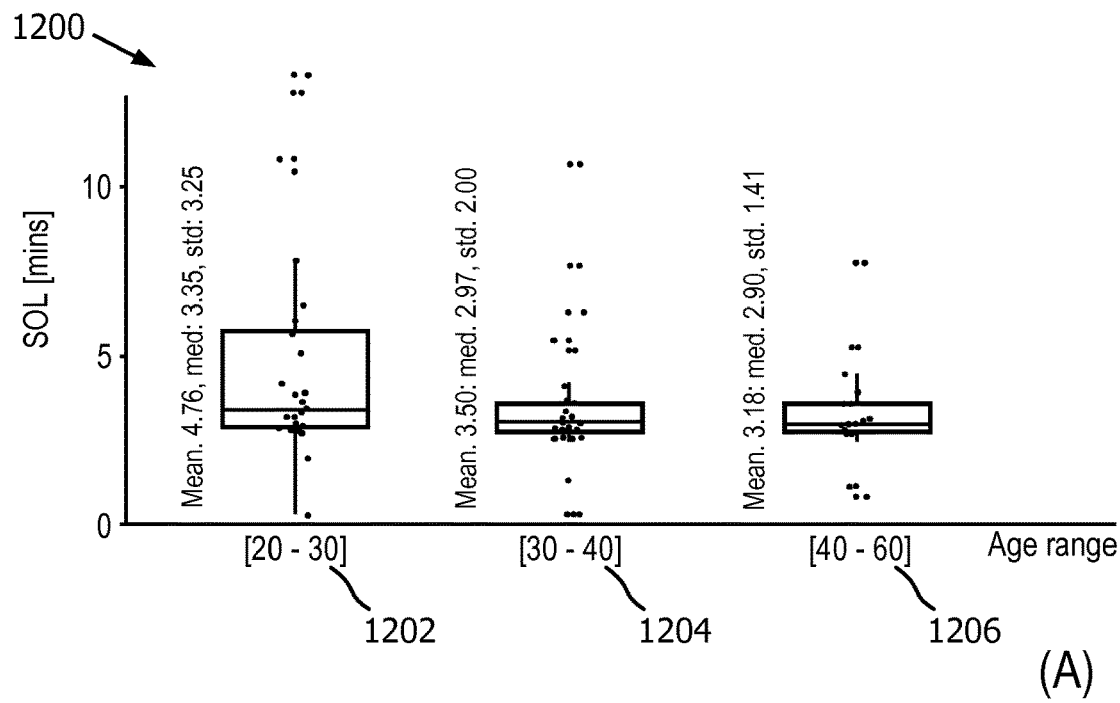
FIG. 12 illustrates determining sleep onset latency points.
Figure 12:
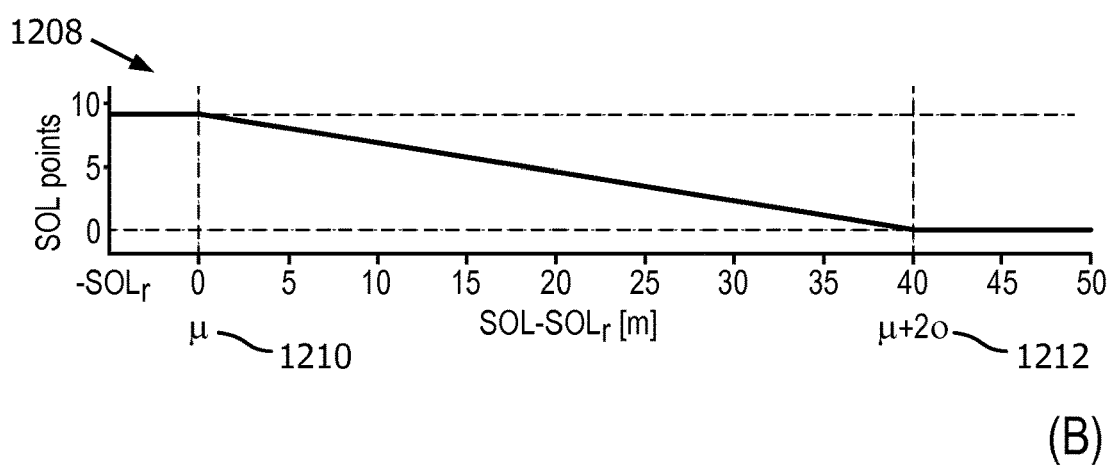
Figure 12:
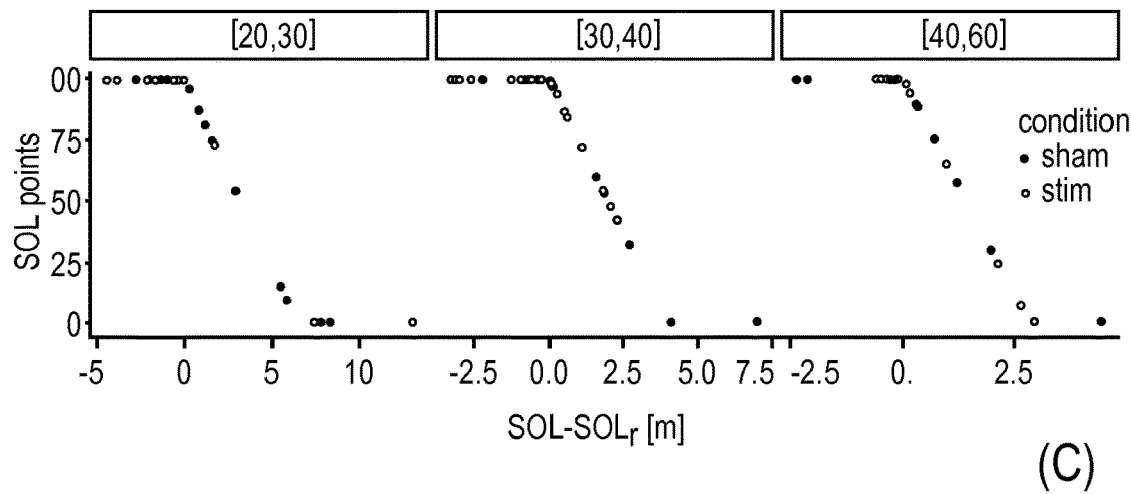

FIG. 12 illustrates determining SOL points (in this example where the indicator is a score) that contribute to the overall determination of the indicator as described herein. FIG. 12(a) illustrates SOL distribution 1200 for three (for example) different age ranges 1202, 1204, 1206 in the age matched reference information. The mean ($\mu$) and standard deviation ($\sigma$) values (e.g., determined by sleep architecture metric component 38 and/or other components of processor 20) for individual age groups are used to determine the number of points associated with SOL according to Equation 8 and FIG. 12(b).

$$SOL \text{ points} = \min\left\{1, \max\left\{0, \frac{\mu - SOL_i + 2*\sigma}{2*\sigma}\right\}\right\} * W_{SOL} * 100 \quad (8)$$

As shown in FIG. 12(b), sleep architecture metric component 38 is configured such that $W_{SOL}$ points 1208 are given if the SOL is at the age matched mean $\mu$ 1210. A linearly decreasing number of points are given if the SOL is within two standard deviations of the age matched mean ($\mu+2*\sigma$)

1212. If the SOL is above $\mu+2*\sigma$, then the number of points assigned is 0. This method penalizes long SOL. In Equation 8, $SOL_i$ is the SOL for a particular sleep session, and $\mu$ and $\sigma$ are the mean and standard deviation for the corresponding age range. The SOL points using this model for the individual example age ranges are show in FIG. 12(c).

Figure 13:
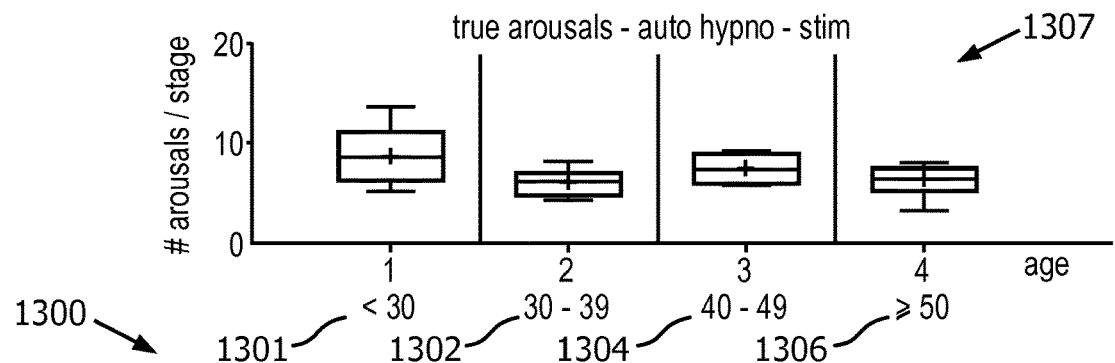
FIG. 13 illustrates arousal points.
Figure 13:
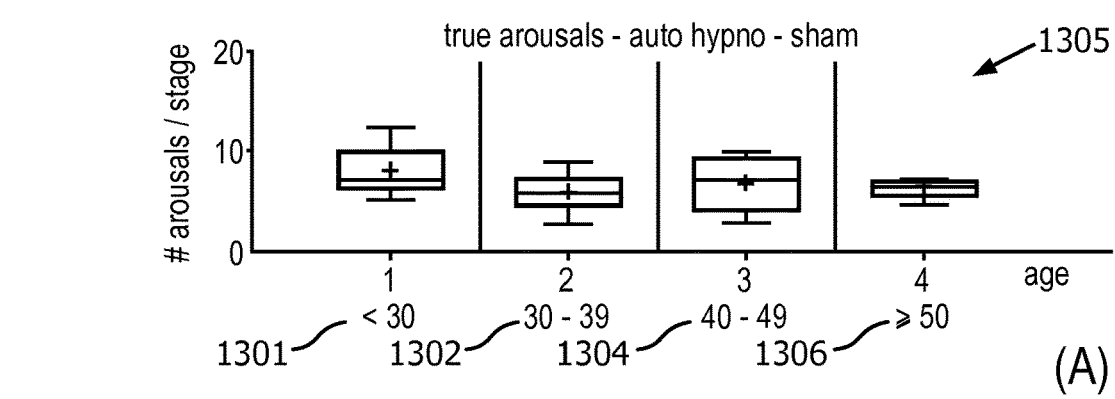
Figure 13:
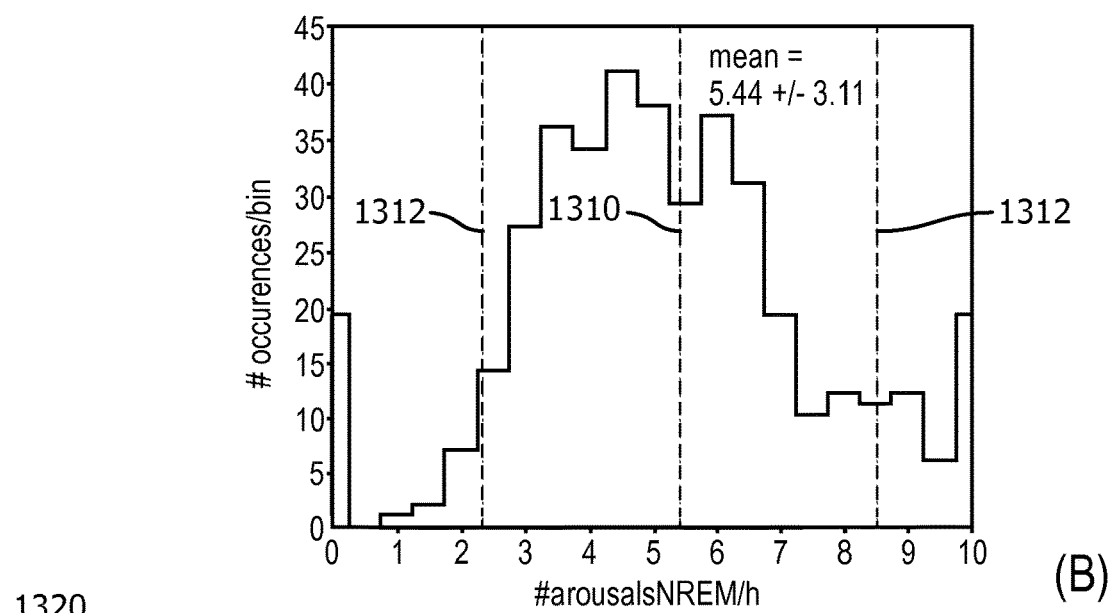
Figure 13:
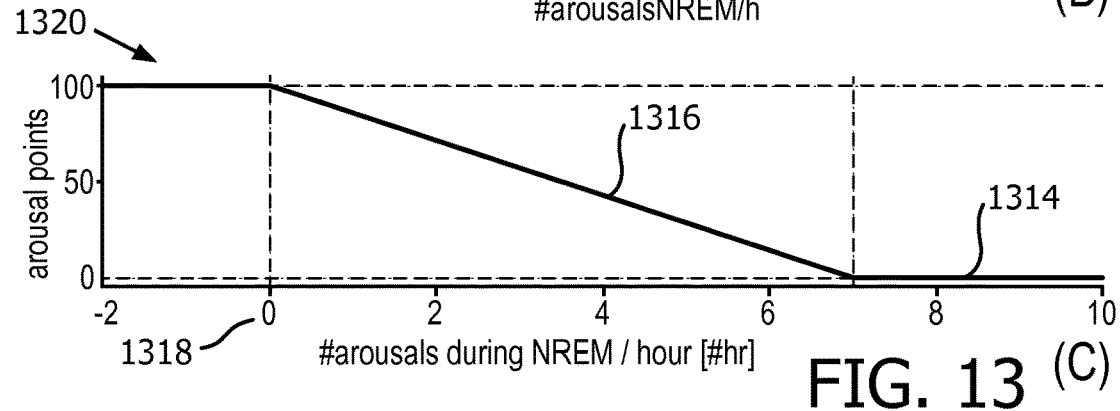

FIG. 13 illustrates determining arousal and/or arousal density points (in this example where the indicator is a score) that contribute to the overall determination of the indicator as described herein. FIG. 13(a) illustrates arousal density (e.g., arousals per hour) distribution 1300 for four (for example) different age ranges 1301, 1302, 1304, 1306 in the age matched reference information. FIG. 13(a) illustrates arousal density 1300 for sham (no stimulation provided) 1305 and stimulated 1307 sleep sessions. The distribution 1300 shows little difference depending on age range and/or condition (sham or stimulation). Thus, for the points (in this example) based on arousal density, sleep architecture metric component 38 is configured such that there is no differentiation in determining points based on age range.

Given the distribution described above, sleep architecture metric component 38 is configured to penalize sleep sessions with an arousal density greater than seven (this is a non-limiting example) arousals per hour (e.g., roughly the mean 1310 plus half of a standard deviation 1312 as shown in FIG. 13(b)) with no points 1314, linearly scale the points 1316 contributed by the arousal density up to an ideal zero arousals 1318 during NREM, and award a full 100 points (this is a non-limiting example and could be any number of points that allows system 10 to function as described herein). 1320. This is also described in Equation 9:

$$\text{arousal points} = \max\left\{0, \min\left\{1, 1 - \frac{arousal_{ACTUAL}}{arousal_{MAX}}\right\}\right\} * 100 \quad (9)$$

where $arousal_{ACTUAL}$ is actual arousal density during automatically detected NREM periods measured in number of arousals per hour and $arousal_{MAX}$ is the defined threshold of currently set (e.g., seven) arousals per hour (e.g., determined by sleep architecture metric component 38 and/or other components of processor 20 based on the information in the output signals from sensors 18 and/or other information). Sleep architecture metric component 38 is configured such that the threshold may be determined at manufacture, entered and/or selected by a user (e.g., subject 12 and/or other users) via user interface 24, determined based on previous sleep sessions of subject 12, and/or determined in other ways.

Figure 14:
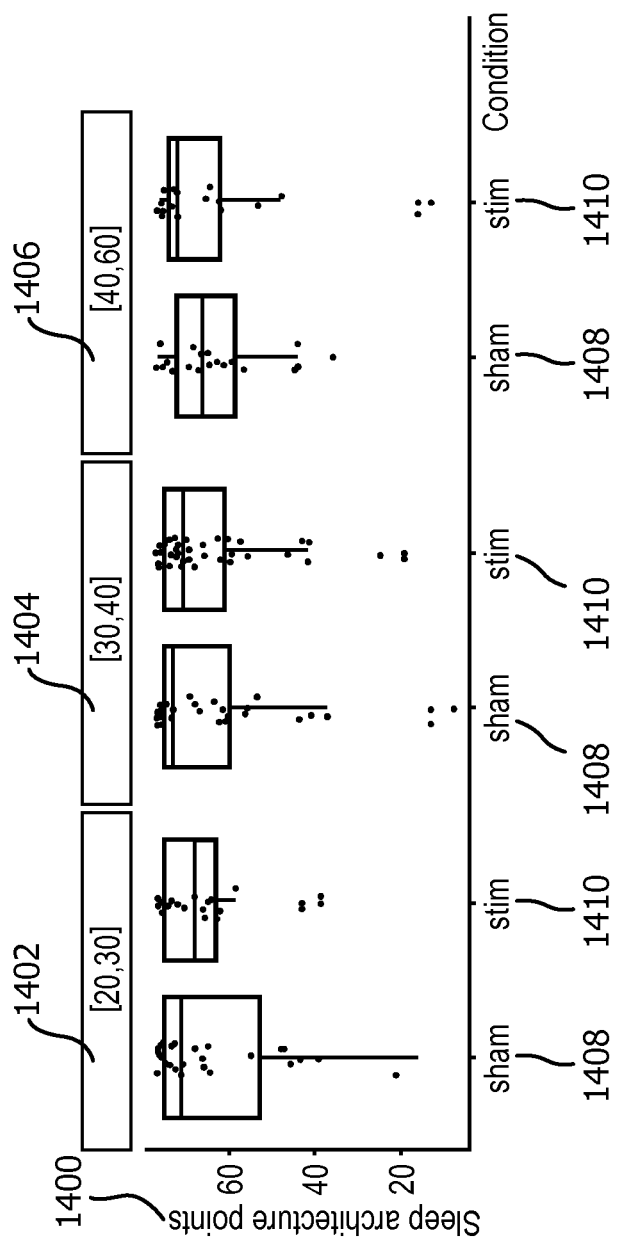
FIG. 14 illustrates example distributions of sleep architecture metrics.

In some embodiments, sleep architecture metric component 38 (FIG. 1) is configured to determine the sleep architecture metric by linearly (for example) combining the TST, WASO, SOL, and arousal points described above based on Equation 10:

$$SA \text{ points} = \frac{a_1 * TST \text{ points} + a_2 * WASO \text{ points} + a_3 * SOL \text{ points} + a_4 * Arousal \text{ points}}{(a_1 + a_2 + a_3 + a_4)} \quad (10)$$

where $a_1$, $a_2$, $a_3$, and $a_4$ are weights assigned by sleep architecture metric component 38 based on a relative importance given to the parameter in question (e.g., determined at manufacture, entered and/or selected by a user (e.g., subject 12 and/or other users) via user interface 24 (FIG. 1), determined based on previous sleep sessions of subject 12, and/or determined in other ways), and TST points, WASO points, SOL points, and Arousal points are the points as described above. By way of a non-limiting example, in some embodiments, sleep architecture metric component 38 may be configured such that $a_1=0.26$, $a_2=0.26$, $a_3=0.09$ and $a_4=0.21$. Example distributions (e.g., by age ranges 1402, 1404, 1406, and sham 1408 versus stimulation 1410) of sleep architecture points (sleep architecture metrics) 1400 determined as detailed above are shown in FIG. 14.

Returning to FIG. 1, combination component 40 is configured to combine the slow wave activity metric, the stimulation quality metric, the sleep architecture metric, and/or other metrics. The metrics are combined to determine the indicator and/or other information. In some embodiments, the combination comprises a linear combination of the slow wave activity metric, the stimulation quality metric, and the sleep architecture metric. In some embodiments, the slow wave activity metric, the stimulation quality metric, and the sleep architecture metric are individually weighted in the linear combination. The combination of the slow wave activity metric, the stimulation quality metric, and the sleep architecture metric is illustrated in FIG. 15.

Figure 15:
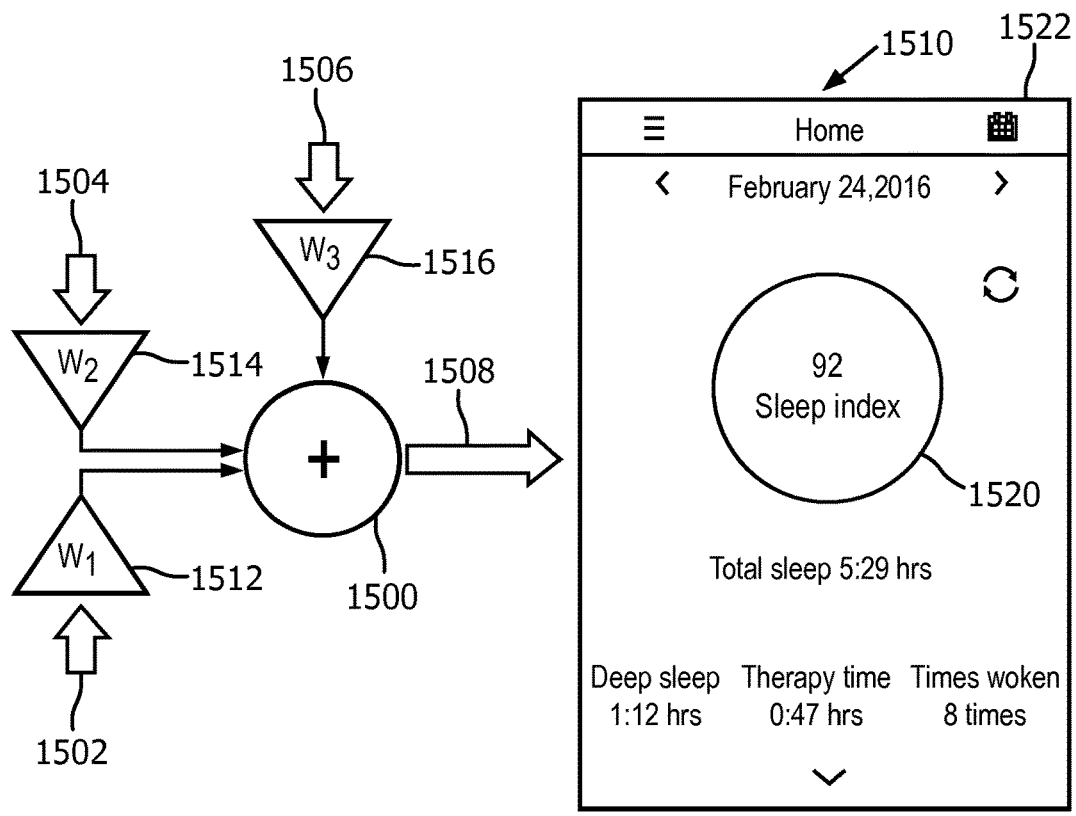
FIG. 15 illustrates combining a slow wave activity metric, a stimulation quality metric, and a sleep architecture metric.

FIG. 15 illustrates combining 1500 slow wave activity metric 1502, stimulation quality metric 1504, and sleep architecture metric 1506 to determine indicator 1508 for display 1510 to subject 12 (FIG. 1). FIG. 15 illustrates display of the indicator as a score 1520 in a graphical user interface 1522 (e.g., user interface 24 shown in FIG. 1) of a computing device (e.g., a smartphone) associated with the user. As shown in FIG. 15, combination component 40 (FIG. 1) is configured such that indicator 1508 is determined as a linear combination of slow wave activity metric 1502, stim quality metric 1504 and sleep architecture metric 1506. The individual metrics (CSWA points corresponds to the slow wave activity metric, stim qty points corresponds to the stimulation quality metric, and SA points corresponds to the sleep architecture metric) are weighted ($W_1$ 1512, $W_2$ 1514, $W_3$ 1516) as shown in FIG. 15 and described in Equation 11.

$$\text{Total score} = w_1 * CSWA \text{ points} + w_2 * \text{stim qty points} + w_3 * SA \text{ points} \quad (11)$$

Weights $W_1$ 1512, $W_2$ 1514, $W_3$ 1516 may be determined at manufacture, entered, selected, and/or adjusted via user interface 24 (e.g., adjusted to achieve a score that best represents the subjective quality of sleep as reported by the users of the system), determined based on previous sleep sessions of subject 12, and/or determined in other ways. In some embodiments, the combined metrics may be equally and/or unequally weighted. For example, in some embodiments, the slow wave activity metric and the stimulation quality metric may be equally weighted, while the sleep architecture metric may be weighted more heavily. As another example, $W_1$ may be about 0.45, $W_2$ may be about 0.05, and $W_3$ may be about 0.5. There are many more possible examples. Combination component 40 may be configured such that the weights described herein have any value that allows system 10 to function as described. In some embodiments, for example to ensure that sham sleep sessions have a total score near 100, combination component 40 may be configured such that the weights are further multiplied by 1.2 (for example) and/or other values. In some embodiments, this is an example of a scaling factor that ensures that sham nights have an average score of 100. In such embodiments, the nights with stimulation will then have scores above 100 which can be more intuitively understood.

Returning to FIG. 1, output component 42 is configured to output the indicator (representative of effects of stimulation provided to subject 12 during the sleep session) for display to subject 12 and/or other users (e.g., doctors, nurses, caregivers, family member, researchers, etc.). Outputting the indicator may comprise wired and/or wireless communication of the indicator, controlling one or more computing devices to display the indicator and/or other outputting.

Figure 16:
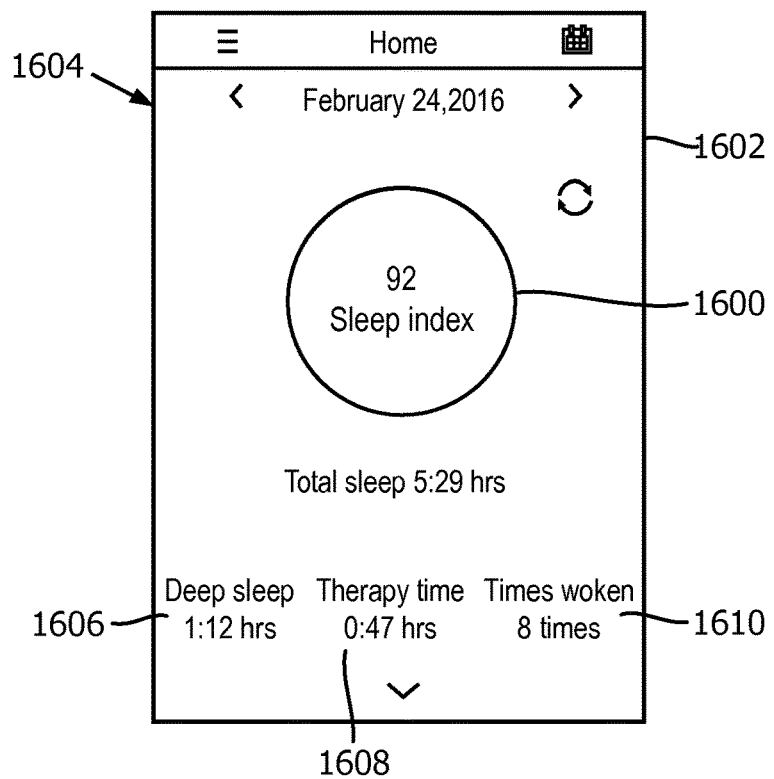
FIG. 16 illustrates an example of displaying the indicator.

FIG. 16 illustrates an example of displaying the indicator to subject 12 and/or other users. FIG. 16 illustrates display of the indicator as a score 1600 in a graphical user interface 1602 (e.g., user interface 24 shown in FIG. 1) of a computing device (e.g., a smartphone) associated with the user. In some embodiments, the score may be a number on a number scale (e.g., 1-100) representative of the benefits of stimulation during sleep. This is not intended to be limiting. In some embodiments, output component 42 may be configured such that the indicator comprises one or more colors, one or more shapes, alphanumeric indicators, letter characters (e.g., A+, B, etc.), sounds (e.g., various beeping (for example) noises and/or other sounds), and/or other characteristics that indicate the benefits of stimulation during sleep to a user (e.g., subject 12). The numbers, colors, shapes, and/or other characteristics may be determined based on the equations and/or other information described above. For example, after a quality night of restorative sleep, output component 42 may be configured to display the indicator as a green circle. After a poor night of sleep, output component 42 may cause display of the indicator as a red circle. These are just examples. Many more possibilities are contemplated (e.g., beeping sounds, etc.). As shown in FIG. 16, graphical user interface 1602 also displays other information including but not limited to the date 1604, a time spent in deep sleep during the sleep session 1606, a therapy time 1608 (e.g., an amount of time stimulation was provided to subject 12), a number of times subject 12 woke from sleep 1610, and/or other information.

Figure 17:
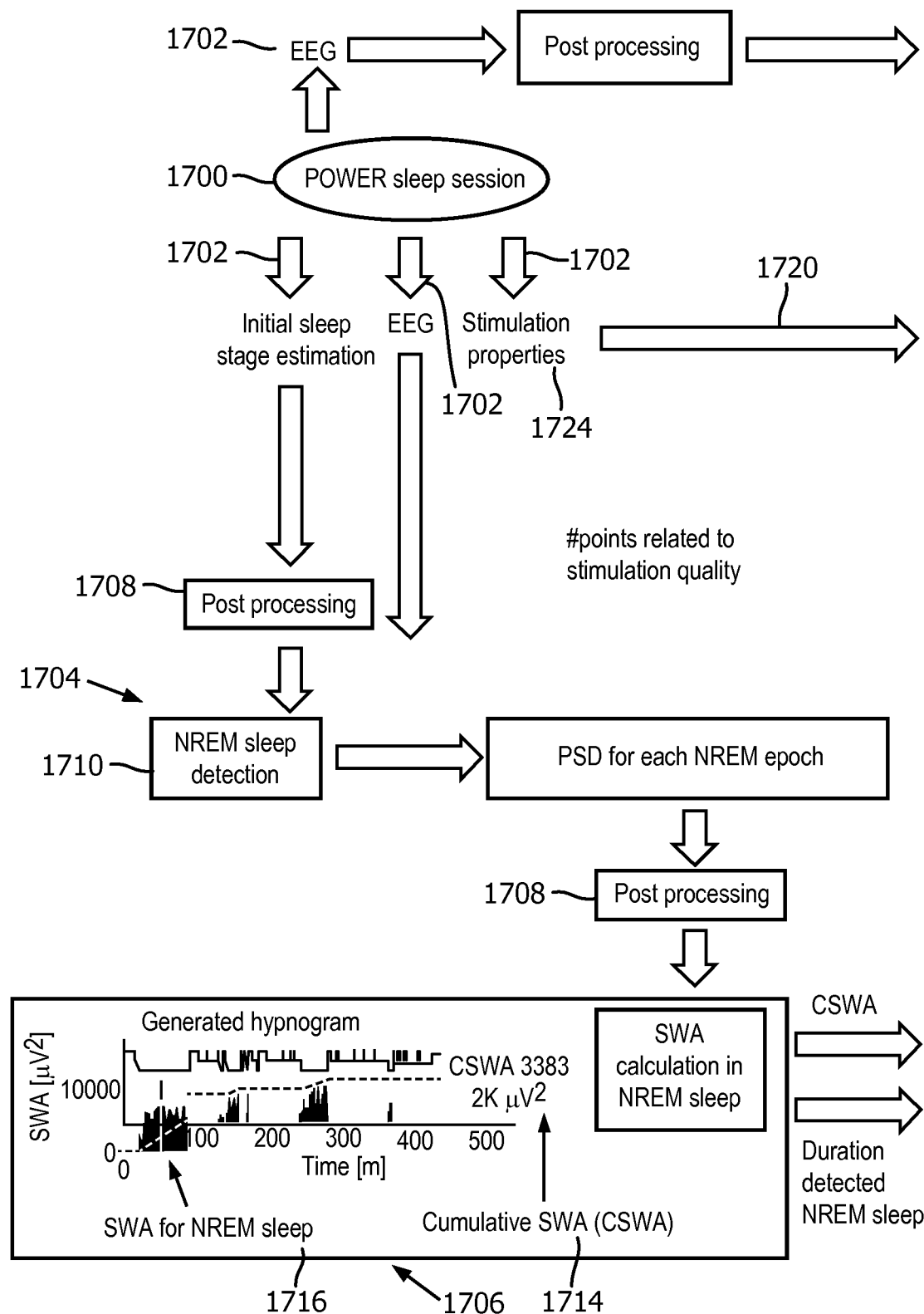
FIG. 17 illustrates examples of operations performed by the system.

FIG. 17 illustrates examples of operations performed by system 10 (FIG. 1). As shown in FIG. 17, system 10 is configured to provide 1700 stimulation to a subject during sleep sessions according to a predetermined therapy regime. Output signals conveying information related to brain activity in the subject and stimulation provided to the subject during the sleep sessions are generated 1702. System 10 is configured such that age matched reference information is obtained for the subject. The age matched reference information for the subject indicates information related to reference amounts of cumulative slow wave activity during sleep sessions, reference levels of stimulation provided during sleep sessions, and reference levels of sleep quality during sleep sessions for a population of subjects similar in age to the subject. At an operation 1704, a slow wave activity metric 1705 is determined. The slow wave activity metric is determined 1706 based on the output signals (e.g., including post processing 1708 EEG information, detecting NREM sleep 1710, etc.), the age matched reference information 1712, and/or other information. In some embodiments, the slow wave activity metric is determined based on a cumulative slow wave activity factor 1714 and a non-rapid eye movement (NREM) duration factor 1716.

At an operation 1720, a stimulation quality metric 1722 is determined. The stimulation quality metric is determined based on the output signals 1702, the stimulation provided to the subject 1724, the age matched reference information 1726, and/or other information. In some embodiments, the stimulation quality metric is determined based on a number of tones delivered to the subject during the sleep session, the age matched reference information, and/or other information.

At an operation 1750, a sleep architecture metric 1751 is determined. The sleep architecture metric is indicative of a sleep quality for the subject during the sleep session. The sleep architecture metric is determined based on the output signals 1702, the age matched reference information 1752, and/or other information. In some embodiments, the sleep architecture metric is determined based on the age matched reference information and one or more of a sleep onset latency value for the subject, a wake after sleep onset value for the subject, a total sleep time during the sleep session, a number of arousals during the sleep session, and/or other information.

At an operation 1760, the slow wave activity metric, the stimulation quality metric, and the sleep architecture metric are combined. The metrics are combined to determine the indicator 1762 and/or other information. In some embodiments, the slow wave activity metric, the stimulation quality metric, and the sleep architecture metric are individually weighted 1764 in the linear combination. At an operation 1780, the indicator (representative of effects of stimulation provided to the subject during the sleep session) is output for display to the subject.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 24 and/or external computing systems, and/or other information that enables system 10 to function properly. For example, electronic storage 22 may store the age matched reference information described herein, the algorithms used to determine the indicator for subject 12, and/or other information. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG, the indicator described herein, and/or other information may be displayed to a caregiver and/or subject 12 via user interface 24. Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices.

In some embodiments, user interface 24 comprises a plurality of separate interfaces. In some embodiments, user interface 24 comprises at least one interface that is provided integrally with processor 20 and/or other components of system 10. In some embodiments, user interface 24 is configured to communicate wirelessly with processor 20 and/or other components of system 10. In some embodiments, as described below, user interface 24 may be included with sensor 18, stimulator 16, processor 20, electronic storage 22 and/or other components of system 10 in a singular device. In some embodiments, user interface 24 may be and/or be included in a computing device such as a desktop computer, a laptop computer, a smartphone, a tablet computer, and/or other computing devices. Such computing devices may run one or more electronic applications having graphical user interfaces configured to provide information to and/or receive information from users. A graphical user interface displayed by a computing device associated with subject 12 may display the indicator to subject 12, for example (e.g., as described above related to output component 42).

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

External resources 26 includes sources of information (e.g., databases, websites, etc. that store the age matched reference information), external entities participating with system 10 (e.g., a medical records system of a health care provider), medical and/or other equipment (e.g., lamps and/or other lighting devices, sound systems, audio and/or visual recording devices, etc.) configured to communicate with and/or be controlled by system 10, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. In some implementations, some or all of the functionality attributed herein to external resources 26 may be provided by resources included in system 10. External resources 26 may be configured to communicate with processor 20, user interface 24, sensor 18, electronic storage 22, sensory stimulator 16, and/or other components of system 10 via wired and/or wireless connections, via a network (e.g., a local area network and/or the internet), via cellular technology, via Wi-Fi technology, and/or via other resources.

In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, these components may be integrated in to a headset and/or other garments worn by subject 12 during sleep.

Figure 18:
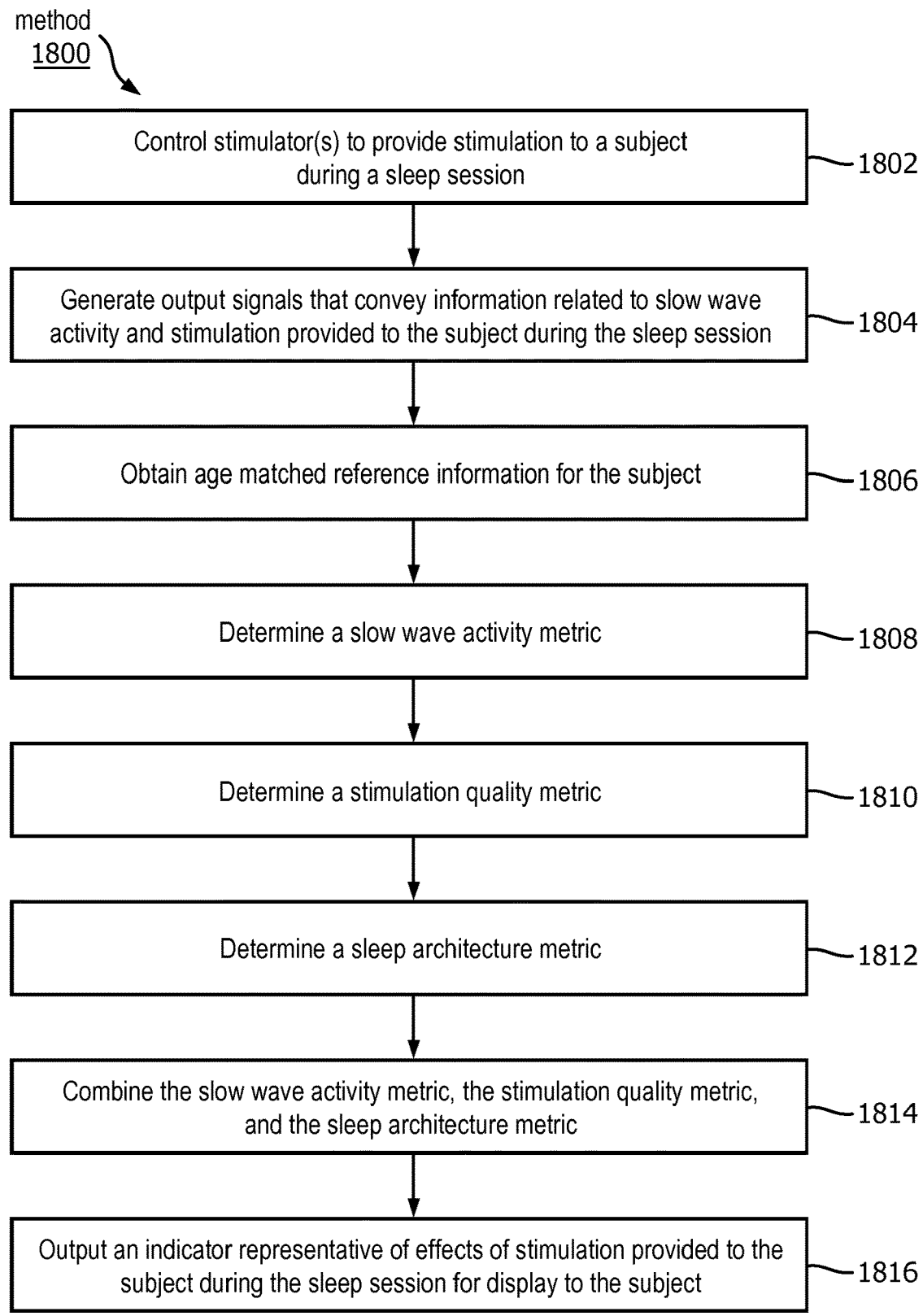
FIG. 18 illustrates a method for outputting an indicator representative of effects of stimulation provided to a subject during a sleep session.

FIG. 18 illustrates a method 1800 for outputting an indicator representative of effects of stimulation provided to the subject during a sleep session with an indicator system. The indicator system comprises one or more stimulators, one or more sensors, one or more hardware processors, and/or other components. The one or more hardware processors are configured to execute computer program components. The computer program components comprise a therapy component, an age matched reference component, a slow wave activity metric component, a stimulation quality metric component, a sleep architecture metric component, a combination component, an output component, and/or other components. The operations of method 1800 presented below are intended to be illustrative. In some embodiments, method 1800 may be accomplished with one or more additional operations not described, and/or without one or more of the operations discussed. Additionally, the order in which the operations of method 1800 are illustrated in FIG. 18 and described below is not intended to be limiting.

In some embodiments, method 1800 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1800 in response to instructions stored electronically on an electronic storage medium. The one or more processing devices may include one or more devices configured through hardware, firmware, and/or software to be specifically designed for execution of one or more of the operations of method 1800.

At an operation 1802, the one or more stimulators are controlled to provide stimulation to a subject during sleep sessions. In some embodiments, the one or more stimulators comprise a tone generator and/or other stimulators. The one or more stimulators are controlled to provide stimulation according to a predetermined therapy regime. In some embodiments, operation 1802 is performed by a processor component the same as or similar to therapy component 30 (shown in FIG. 1 and described herein).

At an operation 1804, output signals conveying information related to brain activity in the subject and stimulation provided to the subject during the sleep sessions are generated. In some embodiments, the one or more sensors comprise electroencephalogram (EEG) sensors and/or other sensors configured to generate EEG output signals conveying information related to brain activity in the subject. In some embodiments, the one or more sensors comprise microphones (for example) and/or other sensors configured to generate output signals conveying information related to the stimulation provided to the subject. In some embodiments, operation 1804 is performed by one or more sensors the same as or similar to sensors 18 (shown in FIG. 1 and described herein).

At an operation 1806, age matched reference information is obtained for the subject. The age matched reference information for the subject indicates information related to reference amounts of cumulative slow wave activity during sleep sessions, reference levels of stimulation provided during sleep sessions, and reference levels of sleep quality during sleep sessions for a population of subjects similar in age to the subject. In some embodiments, operation 1806 is performed by a processor component the same as or similar to age matched reference component 32 (shown in FIG. 1 and described herein).

At an operation 1808, a slow wave activity metric is determined. The slow wave activity metric is indicative of a cumulative amount of slow wave activity in the subject during the sleep session. The slow wave activity metric is determined based on the output signals, the stimulation provided to the subject, the age matched reference information, and/or other information. In some embodiments, the slow wave activity metric is determined based on a cumulative slow wave activity factor and a non-rapid eye movement (NREM) duration factor. In some embodiments, the cumulative slow wave activity and NREM factors are both determined based on the output signals, the age matched reference information, and/or other information. In some embodiments, the cumulative slow wave activity factor is and/or is determined based on cumulative EEG power in a 0.5 to 4 Hz band across detected NREM epochs during the sleep session. In some embodiments, operation 1808 is performed by a processor component the same as or similar to slow wave activity metric component 34 (shown in FIG. 1 and described herein).

At an operation 1810, a stimulation quality metric is determined. The stimulation quality metric is indicative of how well the stimulation enhances slow wave activity in the subject during the sleep session. The stimulation quality metric is determined based on the output signals, the stimulation provided to the subject, the age matched reference information, and/or other information. In some embodiments, the stimulation quality metric is determined based on a number of tones delivered to the subject during the sleep session, the age matched reference information, and/or other information. In some embodiments, operation 1810 is performed by a processor component the same as or similar to stimulation quality metric component 36 (shown in FIG. 1 and described herein).

At an operation 1812, a sleep architecture metric is determined. The sleep architecture metric is indicative of a sleep quality for the subject during the sleep session. The sleep architecture metric is determined based on the output signals, the stimulation provided to the subject, the age matched reference information, and/or other information. In some embodiments, the sleep architecture metric is determined based on the age matched reference information and one or more of a sleep onset latency value for the subject, a wake after sleep onset value for the subject, a total sleep time during the sleep session, a number of arousals during the sleep session, and/or other information. In some embodiments, the sleep onset latency value, the wake after sleep onset value, the total sleep time, and/or the number of arousals are determined based on the output signals and/or other information. In some embodiments, operation 1812 is performed by a processor component the same as or similar to sleep architecture metric component 38 (shown in FIG. 1 and described herein).

At an operation 1814, the slow wave activity metric, the stimulation quality metric, and the sleep architecture metric are combined. The metrics are combined to determine the indicator and/or other information. In some embodiments, the combination comprises a linear combination of the slow wave activity metric, the stimulation quality metric, and the sleep architecture metric. In some embodiments, the slow wave activity metric, the stimulation quality metric, and the sleep architecture metric are individually weighted in the linear combination. In some embodiments, operation 1814 is performed by a processor component the same as or similar to combination component 40 (shown in FIG. 1 and described herein).

At an operation 1816, the indicator (representative of effects of stimulation provided to the subject during the sleep session) is output for display to the subject. In some embodiments, operation 1816 is performed by a processor component the same as or similar to output component 42 (shown in FIG. 1 and described herein).

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination

What is claimed is:

1. A system configured to output an indicator representative of effects of stimulation provided to a subject during a sleep session, the system comprising:
   one or more stimulators configured to provide the stimulation to the subject during the sleep session;
   one or more sensors configured to generate output signals conveying information related to brain activity in the subject during the sleep session; and
   one or more hardware processors operatively communicating with the one or more stimulators and the one or more sensors, the one or more hardware processors configured by machine-readable instructions to:
   determine, based on the output signals and the stimulation provided to the subject:
   a slow wave activity metric indicative of a cumulative amount of slow wave activity in the subject during the sleep session, the slow wave activity metric determined based on a cumulative slow wave activity factor and a non-rapid eye movement (NREM) duration factor;
   a stimulation quality metric indicative how well the stimulation enhances slow wave activity in the subject during the sleep session, the stimulation quality metric determined based on one or both of a number of stimulations delivered to the subject during the sleep session and a number of stimulations at a specific intensity delivered to the subject during the sleep session; and
   a sleep architecture metric indicative of a sleep quality for the subject during the sleep session;
   combine the slow wave activity metric, the stimulation quality metric, and the sleep architecture metric to determine the indicator; and output the indicator for display to the subject.

2. The system of claim 1, wherein the one or more hardware processors are further configured to:
obtain age matched reference information for the subject that indicates information related to reference amounts of cumulative slow wave activity during sleep sessions, reference levels of stimulation provided during sleep sessions, and reference levels of sleep quality during sleep sessions for a population of subjects in an age range that the subject is in; and
determine the slow wave activity metric, the stimulation quality metric, and the sleep architecture metric based on the reference information.

3. The system of claim 2, where the one or more sensors comprise electroencephalogram (EEG) electrodes, and wherein the one or more hardware processors are configured such that:
the slow wave activity metric is determined based on the cumulative slow wave activity factor and the NREM duration factor;
the cumulative slow wave activity and NREM duration factors are both determined based on the output signals and the age matched reference information; and
the cumulative slow wave activity factor is determined based on cumulative EEG power in a 0.5 to 4 Hz band or a sub-band within the 0.5 to 4 Hz band across detected NREM epochs during the sleep session.

4. The system of claim 2, wherein the one or more hardware processors are configured such that the stimulation quality metric is determined based on a number of tones delivered to the subject during the sleep session and a number of tones at a specific volume delivered to the subject during the sleep session, and the age matched reference information.

5. The system of claim 2, wherein the one or more hardware processors are configured such that the sleep architecture metric is determined based on the age matched reference information, a sleep onset latency value for the subject, a wake after sleep onset value for the subject, a total sleep time during the sleep session, and a number of arousals during the sleep session, and
wherein the sleep onset latency value, the wake after sleep onset value, the total sleep time, and/or the number of arousals are determined based on the output signals.

6. The system of claim 1, wherein the one or more hardware processors are configured such that the combination comprises a linear combination of the slow wave activity metric, the stimulation quality metric, and the sleep architecture metric; and
the slow wave activity metric, the stimulation quality metric, and the sleep architecture metric are individually weighted in the linear combination.

7. The system of claim 1, wherein the one or more hardware processors are configured to cause display of the slow wave activity metric, the stimulation quality metric, and the sleep architecture metric.

8. A system for outputting an indicator representative of effects of stimulation provided to a subject during a sleep session, the system comprising:
means for providing the stimulation to the subject during the sleep session;
means for generating output signals conveying information related to brain activity in the subject during the sleep session;
means for determining, based on the output signals and the stimulation provided to the subject:
a slow wave activity metric indicative of a cumulative amount of slow wave activity in the subject during the sleep session, the slow wave activity metric determined based on a cumulative slow wave activity factor and a non-rapid eye movement (NREM) duration factor;
a stimulation quality metric indicative of how well the stimulation enhances slow wave activity in the subject during the sleep session, the stimulation quality metric determined based on one or both of a number of stimulations delivered to the subject during the sleep session and a number of stimulations at a specific intensity delivered to the subject during the sleep session; and
a sleep architecture metric indicative of a sleep quality for the subject during the sleep session, the sleep architecture metric determined based on one or more of a sleep onset latency value for the subject, a wake after sleep onset value for the subject, a total sleep time during the sleep session, or a number of arousals during the sleep session;
means for combining the slow wave activity metric, the stimulation quality metric, and the sleep architecture metric to determine the indicator; and
means for outputting the indicator for display to the subject.

9. The system of claim 8, further comprising:
means for obtaining age matched reference information for the subject that indicates information related to reference amounts of cumulative slow wave activity during sleep sessions, reference levels of stimulation provided during sleep sessions, and reference levels of sleep quality during sleep sessions for a population of subjects in an age range that the subject is in; and
means for determining the slow wave activity metric, the stimulation quality metric, and the sleep architecture metric based on the reference information.

10. The system of claim 9, where the means for generating output signals comprise electroencephalogram (EEG) electrodes, and wherein:
the slow wave activity metric is determined based on the cumulative slow wave activity factor and the NREM duration factor;
the cumulative slow wave activity and NREM duration factors are both determined based on the output signals and the age matched reference information; and
the cumulative slow wave activity factor is determined based on cumulative EEG power in a 0.5 to 4 Hz band or a sub-band within the 0.5 to 4 Hz band across detected NREM epochs during the sleep session.

11. The system of claim 9, wherein the stimulation quality metric is determined based on a number of tones delivered to the subject during the sleep session and a number of tones at a specific volume delivered to the subject during the sleep session, and the age matched reference information.

12. The system of claim 9, wherein the sleep architecture metric is determined based on the age matched reference information, the sleep onset latency value for the subject, the wake after sleep onset value for the subject, the total sleep time during the sleep session, and the number of arousals during the sleep session, and
wherein the sleep onset latency value, the wake after sleep onset value, the total sleep time, and/or the number of arousals are determined based on the output signals.

13. The system of claim 8, wherein the combination comprises a linear combination of the slow wave activity metric, the stimulation quality metric, and the sleep architecture metric; and the slow wave activity metric, the stimulation quality metric, and the sleep architecture metric are individually weighted in the linear combination.

14. The system of claim 8, further comprising means for causing display of the slow wave activity metric, the stimulation quality metric, and the sleep architecture metric.

* * * * *